(12) United States Patent
Son et al.

(10) Patent No.: US 6,713,486 B1
(45) Date of Patent: Mar. 30, 2004

(54) ANTIVIRAL 2,4-PYRIMIDINEDIONE DERIVATIVES AND PROCESS FOR THE PREPARATION THEREOF

(75) Inventors: Jong-Chan Son, Daejeon (KR); Seun-Shil Shin, Jeonju-si (KR); Shin-Keol Kim, Seoul (KR); Chong-Kyo Lee, Daejeon (KR); Hae-Soo Kim, Nonsan-si (KR)

(73) Assignee: Korea Research Institute of Chemical Technology (KR)

( * ) Notice: Subject to any disclaimer, the term of this patent is extended or adjusted under 35 U.S.C. 154(b) by 0 days.

(21) Appl. No.: 09/913,391

(22) PCT Filed: Mar. 3, 2000

(86) PCT No.: PCT/KR00/00166

§ 371 (c)(1),
(2), (4) Date: Aug. 10, 2001

(87) PCT Pub. No.: WO00/51990

PCT Pub. Date: Sep. 8, 2000

(30) Foreign Application Priority Data

Mar. 4, 1999 (KR) .......................................... 1999-7165

(51) Int. Cl.⁷ .................... A61K 31/505; C07D 419/00; C07D 239/02
(52) U.S. Cl. ...................... 514/269; 514/274; 544/300; 544/301; 544/302; 544/303; 544/304; 544/309; 544/310; 544/311; 544/312; 544/313; 544/314
(58) Field of Search ................................. 514/269, 274; 544/310, 311, 312, 309, 300, 301, 302, 303, 304, 313, 314

(56) References Cited

U.S. PATENT DOCUMENTS 5,922,727 A * 7/1999 Cho et al. .................... 514/274

FOREIGN PATENT DOCUMENTS

WO 00/61563 * 10/2000
WO 00/61564 * 10/2000

* cited by examiner

Primary Examiner—Alan L. Rotman
Assistant Examiner—Tamthom N. Truong
(74) Attorney, Agent, or Firm—Anderson Kill & Olick, P.C.

(57) ABSTRACT

2,4-pyrimidinedione derivatives of formula (I) having high antiviral activity against wild-type and mutant HIV-1 and low toxicity are useful for treating AIDS (I) wherein: $R^1$ is a $C_{6-10}$ aryl or $C_{3-10}$ heteroaryl group optionally having one or more substituents selected from the group consisting of halogen, $C_{1-6}$ alkyl, $C_{1-6}$ alkyl substituted with one or more halogen atoms, $C_{3-4}$ cycloalkyl, cyano, nitro, hydroxy, thiohydroxy, azido, $C_{1-6}$ alkoxy, oximino, $C_{1-3}$ alkyloximino, O—($C_{1-6}$ alkyl)-substituted oximino, C—$_{1-6}$ alkylcarbonyl, $C_{3-6}$ cycloalkylcarbonyl, hydroxymethyl, azidomethlyl, $C_{1-6}$ alkoxymethyl, $C_{1-6}$ acyloxynethyl, carbamoyloxymethyl, anminomethyl, N—($C_{1-3}$ alkyl)aminomethyl, N,N-di($C_{1-3}$ alkyl)aminomethyl, carboxy, $C_{1-6}$ alkoxycarbonyl, aziridine, amino, hydroxyethylamino, cyclopropylamino, $C_{1-6}$ alkylamino, di($C_{1-6}$ alkyl)amino, trifluoroacetamido, $C_{1-6}$ acylamido, carbamoyl, hydroxyethylcarbamoyl, cyclopropylcarbamoyl, $C_{1-6}$ alkylcarbamoyl, di($C_{1-6}$ alkyl)carbamoyl, aminocarbamoyl, dimethylaminocarbamoyl, hydrazino, 1,1-dimethylhydrazino, imidazolyl, triazolyl and tetrazolyl; a tetrahydropyridyl or piperidyl group optionally substituted with a $C_{1-6}$ alkyl or $C_{1-6}$ alkoxycarbonyl group; a tetrahydropyranyl group; or a tetrahydrofuryl group; $R^2$ is hydrogen, halogen, nitro, cyano, $C_{1-3}$ alkoxycarbonyl, $C_{1-3}$ alkylamino, di($C_{1-3}$ alkyl)amino, $C_{1-3}$ alkylcarbamol, di($C_{1-3}$ alkyl)carbamoyl, $C_{1-3}$ alkyl, $C_{3-6}$ cycloalkyl or benzyl; $R^3$ and $R^4$ are each independently hydrogen, halogen, hydroxy, cyano, nitro, amino acetamido, trifluoroacetamido, azido, $C_{1-3}$ alkyl, C-$_{1-3}$ alkyl substituted with one or more halogen atoms, $C_{1-3}$ alkoxycarbonyl, carbamoyl $C_{1-3}$ alkylcarbamoyl, di($C_{1-3}$ alkyl) carbamoyl or C-$_{1-3}$ alkoxy; A is O or S; and Z is O, S, C═O, NH or $CH_2$.

(I)

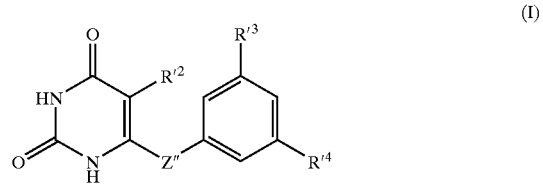

6 Claims, No Drawings

ANTIVIRAL 2,4-PYRIMIDINEDIONE DERIVATIVES AND PROCESS FOR THE PREPARATION THEREOF

This application is a national stage entry under section 371 of PCT/KR00/00166, filed on Mar. 3, 2000.

FIELD OF THE INVENTION

The present invention relates to novel pyrimidinedione derivatives, which are useful as an antiviral agent, particularly for treating acquired immunodeficiency syndrome (AIDS), a process for the preparation thereof and a pharmaceutical composition containing same as an active ingredient.

DESCRIPTION OF THE PRIOR ART

Various compounds such as AZT (3'-azido-3'-deoxythymidine), DDC (2',3'-dideoxycytidine), DDI (2',3'-dideoxyinosine), D4T (3'-deoxy-2',3'-didehydrothymidine) 3TC(lamivudine), Ziagen, Nevirapine, Sustiva, Delavirdine, Indinavir, Ritonavir, Viracept, Saquinavir and Agenerase have been reported to have the ability, albeit limited, to inhibit the reproduction of AIDS virus. However, they are also known to cause undesirable side effects due to their toxicity as well as to induce the mutation of the virus, thereby increasing the resistance of the virus.

In order to minimize such problems, therefore, many attempts have been made. For example, there have been reported 2,4-pyrimidinedione derivatives having 1-alkoxymethyl substituents {J. Med. Chem., 35, 4713 (1992); J. Med. Chem., 35, 337 (1992); J. Med. Chem., 34, 1508 (1991); J. Med. Chem., 34, 1394 (1991); J. Med. Chem., 34, 349 (1991); Molecular Pharm., 39, 805 (1991); Tet. Lett., 35, 4531 (1994); J. Med. Chem., 38, 2860 (1995); Nucleosides and Nucleotides, 14, 575 (1995); J. Med. Chem., 39, 2427 (1996); J. Med. Chem., 42, 4500 (1999); EP 0,449,726 A1; EP 0,420,763 A2; U.S. Pat. No. 5,278,167; U.S. Pat. No. 5,318,972; U.S. Pat. No. 5,461,060; WO95/18109 A1; and U.S. Pat. No. 5,112,835}; 1-allyl or propargyl substituents (U.S. Pat. No. 5,747,500); and 1-cyclopentenylmethylene substituents (U.S. Pat. No. 5,922,727). Although these compounds exhibit improved activity against human immunodeficiency virus (HIV), there exists a need to develope non-toxic compounds having even higher potency against both wild-type and mutant HIV.

SUMMARY OF THE INVENTION

Accordingly, it is a primary object of the present invention to provide a novel compound having superior antiviral activity against both wild-type and mutant HIV-1 as well as reduced toxicity.

It is another object of the present invention to provide a pharmaceutical composition containing same.

It is a further object of the present invention to provide a process for the preparation of said novel compound.

In accordance with one aspect of the present invention, there is provided a novel 2,4-pyrimidinedione compound of formula(I) or a pharmaceutically acceptable salt thereof:

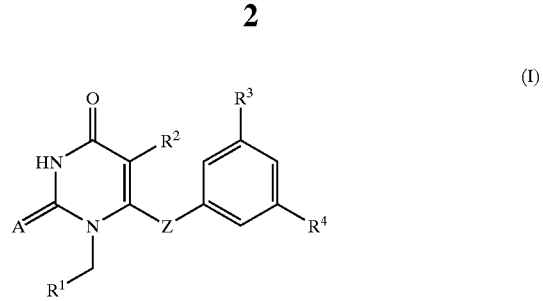

wherein:

$R^1$ is a $C_{6-10}$ aryl or $C_{3-10}$ heteroaryl group optionally having one or more substituents selected from the group consisting of halogen, $C_{1-6}$ alkyl, $C_{1-6}$ alkyl substituted with one or more halogen atoms, $C_{3-6}$ cycloalkyl, cyano, nitro, hydroxy, thiohydroxy, azido, $C_{1-6}$ alkoxy, oximino, $C_{1-3}$ alkyloximino, O—($C_{1-6}$ alkyl)-substituted oximino, $C_{1-6}$ alkylcarbonyl, $C_{3-6}$ cycloalkylcarbonyl, hydroxymethyl, azidomethyl, $C_{1-6}$ alkoxymethyl, $C_{1-6}$ acyloxymethyl, carbamoyloxymethyl, aminomethyl, N—($C_{1-3}$ alkyl)aminomethyl, N,N-di($C_{1-3}$ alkyl)aminomethyl, carboxy, $C_{1-6}$ alkoxycarbonyl, aziridine, amino, hydroxyethylamino, cyclopropylamino, $C_{1-6}$ alkylamino, di($C_{1-6}$ alkyl)amino, trifluoroacetamido, $C_{1-6}$ acylamido, carbamoyl, hydroxyethylcarbamoyl, cyclopropylcarbamoyl, $C_{1-6}$ alkylcarbamoyl, di($C_{1-6}$ alkyl)carbamoyl, aminocarbamoyl, dimethylaminocarbamoyl, hydrazino, 1,1-dimethylhydrazino, imidazolyl, triazolyl and tetrazolyl; a tetrahydropyridyl or piperidyl group optionally substituted with a $c_{1-6}$ alkyl or $c_{1-6}$ alkoxycarbonyl group; a tetrahydropyranyl group; or a tetrahydrofuryl group;

$R^2$ is hydrogen, halogen, nitro, cyano, $C_{1-3}$ alkoxycarbonyl, $C_{1-3}$ alkylamino, di($C_{1-3}$ alkyl)amino, $C_{1-3}$ alkylcarbamoyl, di($C_{1-3}$ alkyl)carbamoyl, $C_{1-6}$ alkyl, $C_{3-6}$ cycloalkyl or benzyl;

$R^3$ and $R^4$ are each independently hydrogen, halogen, hydroxy, cyano, nitro, amino, acetamido, trifluoroacetamido, azido, $C_{1-3}$ alkyl, $C_{1-3}$ alkyl substituted with one or more halogen atoms, $C_{1-3}$ alkoxycarbonyl, carbamoyl, $C_{1-3}$ alkylcarbamoyl, di($C_{1-3}$ alkyl)carbamoyl or $C_{1-3}$ alkoxy;

A is O or S; and

Z is O, S, C=O, NH or $CH_2$.

DETAILED DESCRIPTION OF THE INVENTION

Among the compounds of formula(I) of the present invention, the preferred are those wherein $R^1$ is a phenyl, pyridyl or N-oxopyridyl group optionally having one or more substituents as listed in formula(I).

The 2,4-pyrimidinedione compound of formula(I) may be prepared by coupling a compound of formula(II) with a compound of formula(III), as shown in the Reaction Scheme A:

Reaction Scheme A

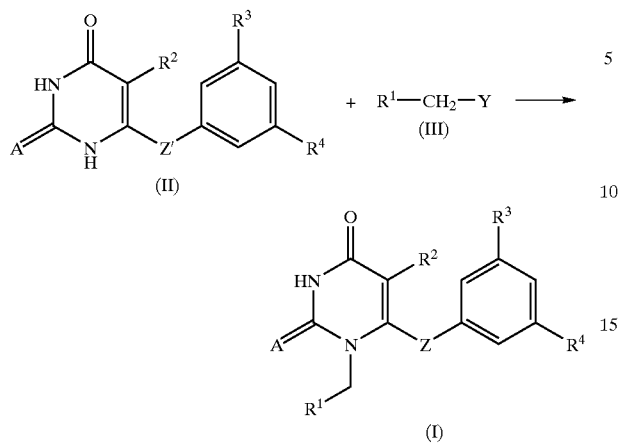

wherein:
- $R^1$, $R^2$, $R^3$, $R^4$, A and Z have the same meanings as defined in formula(I) above;
- Z' is same as Z with the proviso that when A is oxygen, it can be a acetamido group; and
- Y is a suitable leaving group, e.g., halogen, methanesulfonyl, toluenesulfonyl or trifluoromethane-sulfonyl.

In Reaction Scheme A, the above reaction may be conducted in a solvent in the presence of a base at a temperature ranging from −10 to 100° C., wherein the molar ratio of the compound of formula(II) to the compound of formula(III) may range from 1:0.8 to 1:1.2. Representative examples of the base include lithium hydride, sodium hydride, potassium hydride, sodium carbonate, potassium carbonate and the like. Suitable for use in this reaction is a polar solvent such as acetonitrile, hexamethylphosphoramide (HMPA), dimethylsulfoxide (DMSO) and dimethylformamide(DMF).

The compounds of formula(II) may in some cases be prepared in accordance with the procedure disclosed in U.S. Pat. No. 5,747,500. Alternatively, the compounds of formula (II) may be advantageously prepared in some special cases by the procedure illustrated in Reaction Scheme B:

Reaction Scheme B

Method (i): Useful when A is O and Z' is acetamido

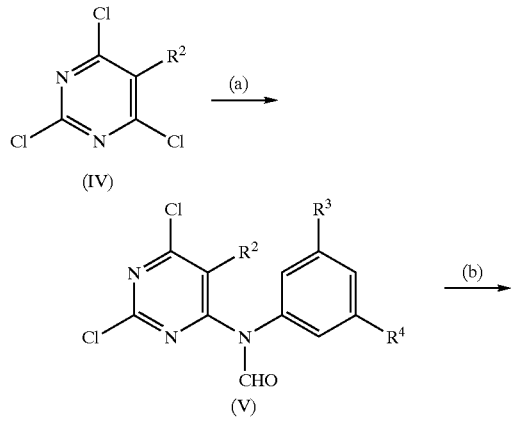

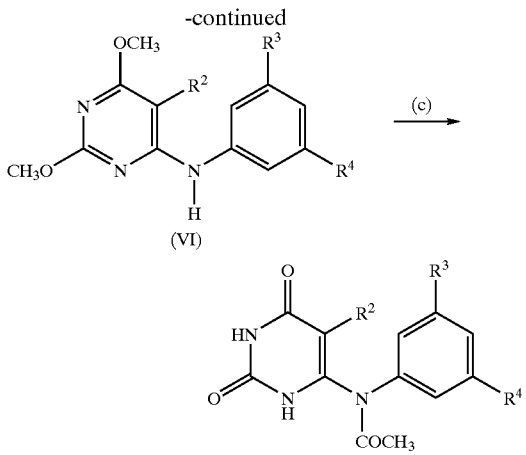

Method (ii): Useful when A is O, Z' is C=O and $R^3$(or $R^4$) is $NO_2$

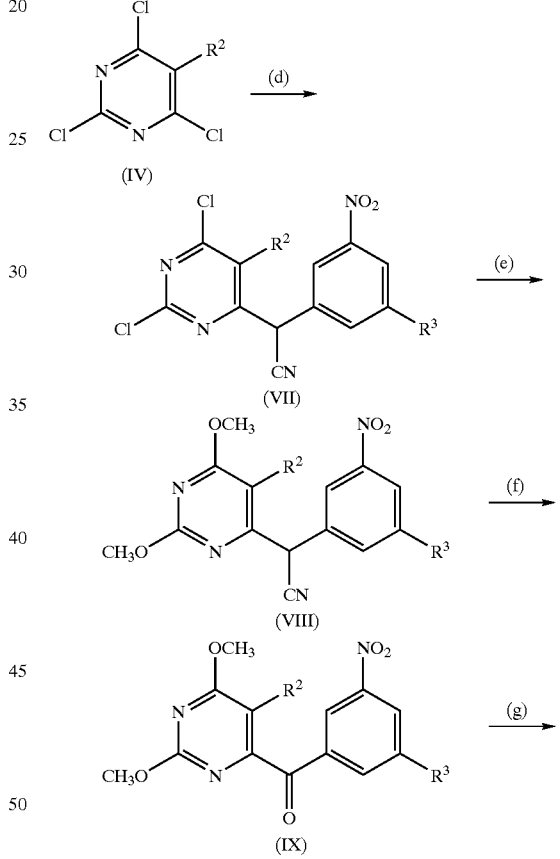

wherein, $R^2$, $R^3$ and $R^4$ have the same meanings as defined in formula (I).

In accordance with the method (i) in Reaction Scheme B, a compound of formula(IV) which may be prepared by way of a known method disclosed in, e.g., *Ber.*, 52B, 869 (1919) and *J. Med. Chem.*, 7, 808 (1964), is subjected to a coupling reaction with an arylformamide derivative in a polar solvent, e.g., dimethylformamide, in the presence of a strong base, e.g., sodium hydride, under a nitrogen atmosphere to provide a compound of formula(V) (Step (a)). The compound of formula (V) is reacted with sodium methoxide in methanol to give a compound of formula(VI) (Step (b)). Then, the compound of formula(VI) is demethylated and acetylated by the action of acetylbromide to provide a compound of formula(II-a) (Step (c)).

In the method (ii) of Reaction Scheme B, the compound of formula (IV) is reacted with a arylacetonitrile derivative in a polar solvent, e.g., dimethylformamide, in the presence of a base, e.g., sodium hydride, to provide a compound of formula(VII) (Step (d)), which is reacted with sodium methoxide in methanol to give a compound of formula(VIII) (Step (e)). Thereafter, the compound of formula(VIII) is reacted with a base, e.g., sodium hydride, in a polar solvent, e.g., dimethylformamide, in the presence of oxygen to provide a compound of formula(IX) (Step (f)), which is hydrolyzed with an acid, e.g., hydrochloric acid, to provide a compound of formula(II-b) (Step (g)).

Each of the compounds of formula(II-a) and (II-b) may be converted to one of the compounds of formula(II) containing various substituents via further reactions.

In this regard, in accordance with another aspect of the present invention, there is provided a compound of formula (II):

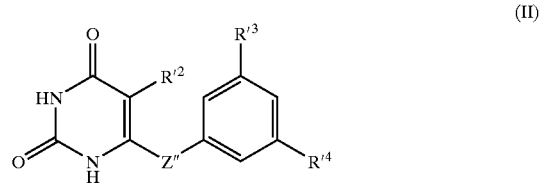

(II)

wherein:

$R'^2$ is ethyl or isopropyl;

$R'^3$ is nitro, amino, acetamido, trifluoroacetamido or $C_{1-3}$ alkoxycarbonyl;

$R'^4$ is methyl or halogen; and $Z''$ is C=O, NH or acetamido.

Exemplary compounds of formula(I) of the present invention which can be prepared in accordance with the methods described above are listed in the following Table 1:

TABLE 1

| Comp. | A | Z | $R^1$ | $R^2$ | $R^3$ | $R^4$ |
|---|---|---|---|---|---|---|
| 1 | O | C=O | 4-pyridyl | Isopropyl | $CH_3$ | $CH_3$ |
| 2 | O | C=O | 3-pyridyl | Isopropyl | $CH_3$ | $CH_3$ |
| 3 | O | C=O | 2-pyridyl | Isopropyl | $CH_3$ | $CH_3$ |
| 4 | O | C=O | 4-pyridyl | Ethyl | $CH_3$ | $CH_3$ |
| 5 | O | C=O | 3-pyridyl | Ethyl | $CH_3$ | $CH_3$ |
| 6 | O | C=O | 2-pyridyl | Ethyl | $CH_3$ | $CH_3$ |
| 7 | O | C=O | 4-pyridyl | Isopropyl | $CH_3$ | F |
| 8 | O | C=O | 3-pyridyl | Isopropyl | $CH_3$ | F |
| 9 | O | C=O | 2-pyridyl | Isopropyl | $CH_3$ | F |

TABLE 1-continued

| Comp. | A | Z | R¹ | R² | R³ | R⁴ |
|---|---|---|---|---|---|---|
| 10 | O | C=O | 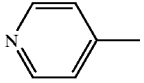 4-pyridyl | Ethyl | CH₃ | F |
| 11 | O | C=O | 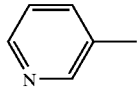 3-pyridyl | Ethyl | CH₃ | F |
| 12 | O | C=O | 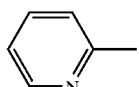 2-pyridyl | Ethyl | CH₃ | F |
| 13 | O | C=O | 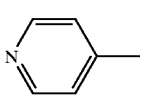 4-pyridyl | Isopropyl | F | F |
| 14 | O | C=O | 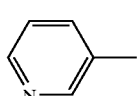 3-pyridyl | Isopropyl | F | F |
| 15 | O | C=O | 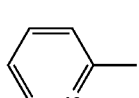 2-pyridyl | Isopropyl | F | F |
| 16 | O | C=O | 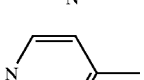 4-pyridyl | Ethyl | F | F |
| 17 | O | C=O |  3-pyridyl | Ethyl | F | F |
| 18 | O | C=O | 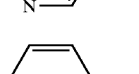 2-pyridyl | Ethyl | F | F |
| 19 | O | C=O | 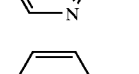 4-pyridyl | Isopropyl | Cl | Cl |
| 20 | O | C=O | 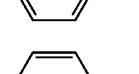 4-pyridyl | Ethyl | Cl | Cl |
| 21 | O | C=O | 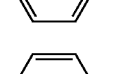 4-pyridyl | Isopropyl | CH₃ | Cl |
| 22 | O | C=O | 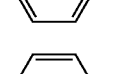 4-pyridyl | Isopropyl | CH₂F | CH₃ |
| 23 | O | C=O | 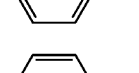 4-pyridyl | Ethyl | CH₂F | CH₃ |
| 24 | O | O | 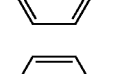 4-pyridyl | Isopropyl | CH₃ | CH₃ |

TABLE 1-continued
| Comp. | A | Z | R¹ | R² | R³ | R⁴ |
|---|---|---|---|---|---|---|
| 25 | O | O | 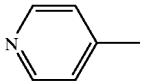 | Ethyl | $CH_3$ | $CH_3$ |
| 26 | O | S | 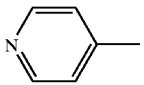 | Isopropyl | Cl | Cl |
| 27 | O | S | 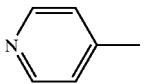 | Isopropyl | $CH_3$ | $CH_3$ |
| 28 | O | S | 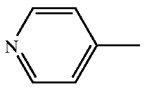 | Ethyl | $CH_3$ | $CH_3$ |
| 29 | O | C=O | 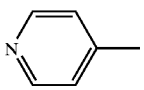 | Isopropyl | $CF_3$ | $CF_3$ |
| 30 | O | C=O | 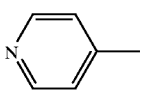 | Ethyl | $CF_3$ | $CF_3$ |
| 31 | O | C=O | 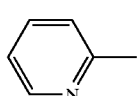 | Isopropyl | $CF_3$ | $CF_3$ |
| 32 | O | C=O | 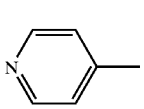 | Isopropyl | $CH_3$ | H |
| 33 | O | C=O | 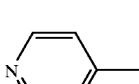 | Ethyl | $CH_3$ | H |
| 34 | O | C=O | 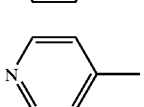 | Isopropyl | H | H |
| 35 | O | C=O | 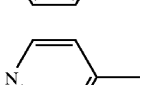 | Ethyl | H | H |
| 36 | O | C=O | 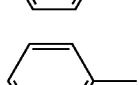 | Isopropyl | $CH_3$ | $CH_3$ |
| 37 | O | C=O | 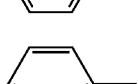 | Ethyl | $CH_3$ | $CH_3$ |
| 38 | O | C=O | 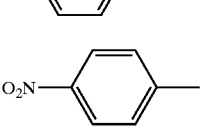 | Isopropyl | $CH_3$ | $CH_3$ |
| 39 | O | C=O | 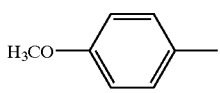 | Isopropyl | $CH_3$ | $CH_3$ |

TABLE 1-continued

| Comp. | A | Z | R¹ | R² | R³ | R⁴ |
|---|---|---|---|---|---|---|
| 40 | O | C=O | 3,5-dimethyl-4-chlorophenyl (H₃C, CH₃, Cl) | Isopropyl | CH₃ | CH₃ |
| 41 | O | C=O | 4-nitrophenyl (O₂N-C₆H₄-) | Ethyl | CH₃ | CH₃ |
| 42 | O | C=O | 4-methoxyphenyl (H₃CO-C₆H₄-) | Ethyl | CH₃ | CH₃ |
| 43 | O | C=O | 3,5-difluorophenyl | Isopropyl | CH₃ | CH₃ |
| 44 | O | C=O | 3,5-bis(trifluoromethyl)phenyl | Isopropyl | CH₃ | CH₃ |
| 45 | O | C=O | 2-methylpyridin-4-yl (H₃C-pyridyl) | Isopropyl | CH₃ | CH₃ |
| 46 | O | C=O | 2-methylpyridin-4-yl | Isopropyl | CH₃ | F |
| 47 | O | C=O | 2-methylpyridin-4-yl | Isopropyl | CH₃ | Cl |
| 48 | O | C=O | 2-methylpyridin-4-yl | Isopropyl | Cl | Cl |
| 49 | O | C=O | 2-methylpyridin-4-yl | Isopropyl | CH₂F | CH₃ |

TABLE 1-continued
| Comp. | A | Z | R¹ | R² | R³ | R⁴ |
|---|---|---|---|---|---|---|
| 50 | O | C=O | 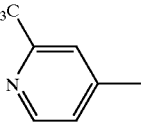 | Isopropyl | CH₃ | H |
| 51 | O | C=O | 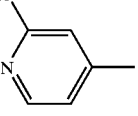 | Isopropyl | CH₃ | CH₃ |
| 52 | O | C=O | 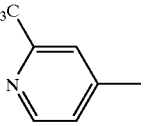 | Ethyl | CH₃ | CH₃ |
| 53 | O | C=O | 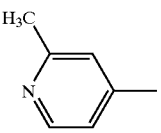 | Ethyl | CH₃ | F |
| 54 | O | C=O | 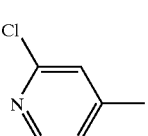 | Ethyl | CH₃ | CH₃ |
| 55 | O | C=O | 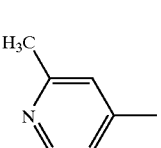 | Isopropyl | CH₃ | CH₃ |
| 56 | O | C=O | 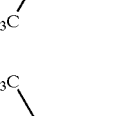 | Isopropyl | F | F |
| 57 | O | C=O | 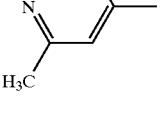 | Isopropyl | Cl | Cl |
| 58 | O | C=O | 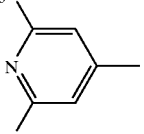 | Isopropyl | CH₂F | CH₃ |

TABLE 1-continued
| Comp. | A | Z | R¹ | R² | R³ | R⁴ |
|---|---|---|---|---|---|---|
| 59 | O | C=O | 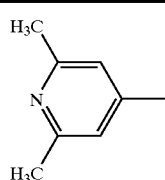 | Isopropyl | Cl | CH₃ |
| 60 | O | C=O | 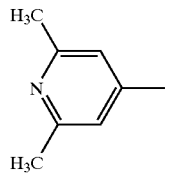 | Ethyl | CH₃ | CH₃ |
| 61 | O | C=O | 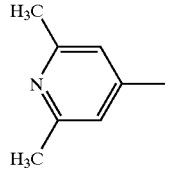 | Ethyl | F | F |
| 62 | O | C=O | 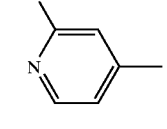 | Isopropyl | CH₃ | CH₃ |
| 63 | O | C=O | 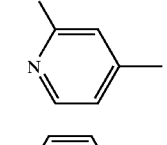 | Isopropyl | CH₃ | Cl |
| 64 | O | C=O | 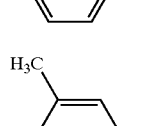 | Isopropyl | CH₃ | NO₂ |
| 65 | O | C=O | 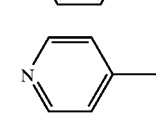 | Isopropyl | CH₃ | NO₂ |
| 66 | O | NH |  | Isopropyl | CH₃ | CH₃ |
| 67 | O | NH | 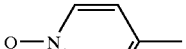 | Ethyl | CH₃ | CH₃ |
| 68 | O | C=O |  | Isopropyl | CH₃ | CH₃ |
| 69 | O | C=O | 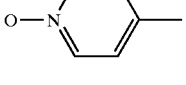 | Isopropyl | CH₃ | CH₃ |

TABLE 1-continued

| Comp. | A | Z | R¹ | R² | R³ | R⁴ |
|---|---|---|---|---|---|---|
| 70 | O | C=O | 2,6-dimethyl-pyridin-4-yl N-oxide | Isopropyl | CH₃ | CH₃ |
| 71 | O | C=O | 2,6-dimethyl-pyridin-4-yl N-oxide | Isopropyl | CH₃ | Cl |
| 72 | O | C=O | 2-(AcOCH₂)-pyridin-4-yl | Isopropyl | CH₃ | CH₃ |
| 73 | O | C=O | 2-methyl-6-(AcOCH₂)-pyridin-4-yl | Isopropyl | CH₃ | CH₃ |
| 74 | O | C=O | 2-methyl-6-(AcOCH₂)-pyridin-4-yl | Isopropyl | CH₃ | Cl |
| 75 | O | C=O | 2-(HOCH₂)-pyridin-4-yl | Isopropyl | CH₃ | CH₃ |
| 76 | O | C=O | 2-methyl-6-(HOCH₂)-pyridin-4-yl | Isopropyl | CH₃ | CH₃ |
| 77 | O | C=O | 2-methyl-6-(HOCH₂)-pyridin-4-yl | Isopropyl | CH₃ | Cl |
| 78 | O | C=O | 2-(CH₃O₂C)-pyridin-4-yl | Isopropyl | CH₃ | CH₃ |

TABLE 1-continued

| Comp. | A | Z | R¹ | R² | R³ | R⁴ |
|---|---|---|---|---|---|---|
| 79 | O | C=O | NH₂OC-(pyridyl)- | Isopropyl | $CH_3$ | $CH_3$ |
| 80 | O | C=O | NH₂OC-(pyridyl)- | Isopropyl | $CH_3$ | Cl |
| 81 | O | C=O | H₂N-(phenyl)- | Isopropyl | $CH_3$ | $CH_3$ |

Furthermore, the present invention encompasses, within its scope, pharmaceutically acceptable salts of the 2,4-pyrimidinedione compounds of formula(I). Suitable pharmaceutically acceptable salts of the compounds of formula (I) possessing strong antiviral activity against wild-type and mutant HIV-1 may include alkali or alkaline earth metal salts, e.g., sodium, potassium, magnesium and calcium salts thereof.

The present invention also includes within its scope pharmaceutical compositions comprising one or more of the compounds of formula(I) or their above-mentioned salts as the active ingredient, in association with pharmaceutically acceptable carriers, excipients or other additives, if necessary.

The pharmaceutical compositions of the invention may be formulated for administration orally or by injection. The composition for oral administration may take various forms such as tablets and gelatin capsules, which may contain conventional additives such as a diluent (e.g., lactose, dextrose, sucrose, mannitol, sorbitol, cellulose and glycine), a lubricant (e.g., silica, talc, stearic acid or its magnesium and calcium salts and polyethylene glycol). In the case of the tablet form, the composition may further comprise a binder (e.g., magnesium aluminum silicate, starch paste, gelatin, tragacanth, methyl cellulose, sodium carboxymethyl cellulose and polyvinyl pyrrolidone) and optionally a disintegrant (e.g., starch, agar and alginic acid or its sodium salt), absorbant, colorant, flavor, sweetener and the like. The composition for injection may be an isotonic solution or a suspension.

The composition may be sterilized and/or contain an adjuvant such as a preservative, stabilizer, wetting agent, emulsifier, a salt for controlling an osmotic pressure and/or a buffer solution, and other pharmaceutically effective materials.

The pharmaceutical compositions can be prepared by a conventional mixing, granulating or coating method and may contain preferably about 0.1 to 75%, more preferably about 1 to 50% of the active ingredient of this invention. The unit dosage of the composition suitable for administering a person weighing about 50 to 70 kg may contain about to 200 mg of the active ingredient.

The following Preparations and Examples are given for the purpose of illustration only and are not intended to limit the scope of the invention.

In the Preparations and Examples, unless otherwise specified, the evaporation was conducted under reduced pressure, preferably under a pressure ranging from about to 100 mmHg.

Preparations

The compounds of formula(II) having the structures (A) to (U), (II-a-1), (II-a-2) and (II-b-1) shown in Table 2 together with their melting points and NMR data were used in preparing respective compounds of formula (I) of the present invention.

Preparations 1 to 21

Each of the compounds having the specified structures (A) to (U) was prepared in accordance with the procedure described in U.S. Pat. No. 5,747,500.

Preparation 22: Synthesis of 5-Isopropyl-6-(3',5'-dimethylphenylacetamido)-2,4-pyrimidinedione (Compound (II-a-1))

Step 1) Synthesis of 2,4-Dichloro-5-isopropyl-6-(3',5'-dimethylphenylformylamido)pyrimidine To a magnetically stirred DMF solution (80 ml) of 3,5-dimethylformaniline (8.94 g, 60 mmol) cooled in an ice bath, 60% sodium hydride dispersion (2.88 g, 72 mmol) was added portionwise under a nitrogen atmosphere. After 10 min, 5-isopropyl-2,4,6-trichloropyrimidine (16.2 g, 72 mmol) was added thereto and the reaction mixture was allowed to warm to room temperature, followed by stirring for 24 hr. Ether was then added to the reaction mixture, and the organic layer was washed with water, dried over anhydrous magnesium sulfate, and filtered. The solvent was removed under reduced pressure and the resulting residue was purified by flash chromatography (eluent-ether:hexane=1:15) to afford 3.3 g (yield 17%) of the title compound as a white solid.

M.p.: 151 to 153° C.; ¹H-NMR (200 MHz, $CDCl_3$) δ 1.12–1.24 (6H, m), 2.30 (6H, s), 3.22 (1H, m), 6.72 (2H, s), 6.96 (1H, s), 8.70 (1H, s); m/z (EI) 338 (M⁺).

Step 2) Synthesis of 2,4-Dimethoxy-5-isopropyl-6-(3',5'-dimethylphenylamino)pyrimidine Sodium (1.02 g, 44 mmol) was added portionwise to a stirred anhydrous methanol (40 ml) at room temperature under a nitrogen atmosphere to prepare sodium methoxide solution. The compound obtained in Step 1) (3 g, 8.88 mmol) was added to the solution and the mixture was refluxed for 4 hr. The reaction mixture was allowed to cool to room temperature and neutralized with excess ammonium chloride. The solvent was removed under reduced pressure and the resulting residue was purified by flash chromatography (eluent-ethyl acetate:hexane=1:15) to afford 2.69 g (yield 97%) of the title compound as a white solid.

M.p.: 126 to 127° C.; $^1$H-NMR (200 MHz, CDCl$_3$) δ 1.31 (6H, d, J=7.1 Hz), 2.31 (6H, s), 3.12 (1H, m), 3.92 (3H, s), 3.93 (3H, s), 6.44 (1H, s), 6.70 (1H, s), 7.21 (2H, s); m/z (EI) 301 (M$^+$).

Step 3) Synthesis of 5-Isopropyl-6-(3',5'-dimethylphenylacetamido)-2,4-pyrimidinedione The compound obtained in Step 2) (2.6 g, 8.6 mmol) was refluxed with acetyl bromide (30 ml) for 19 hr. The reaction mixture was allowed to cool to room temperature and the solvent was removed under reduced pressure. The resulting residue was purified by flash chromat ography (eluent-ethyl acetate:hexane=2:1) to afford 2.6 g (yield 96%) of the title compound as a white solid.

Preparation 23: Synthesis of 5-Ethyl-6-(3',5'-dimethylphenylacetamido)-2,4-pyrimidinedione (Compound (II-a-2))

The procedure of Preparation 22 was repeated using 5-ethyl-2,4,6-trichloropyrimidine in place of 5-isopropyl-2,4,6-trichloropyrimidine to prepare the title compound.

Preparation 24: Synthesis of 5-Isopropyl-6-(3'-nitro-5'-methylbenzoyl)-2,4-pyrimidinedione (Compound (II-b-1))

Step 1) Synthesis of 2,4-Dichloro-5-isopropyl-6-(α-cyano-3'-nitro-5'-methylbenzyl)pyrimidine To a magnetically stirred DMF solution (30 ml) of 3-nitro-5-methylphenylacetonitrile (2.64 g, 15 mmol) and 5-isopropyl-2,4,6-trichloropyrimidine (4.05 g, 18 mmol) cooled in an ice bath, 60% sodium hydride dispersion (1.15 g, 30 mmol) was added portionwise under a nitrogen atmosphere. After stirring for 2 hr, the reaction mixture was allowed to warm to room temperature and stirred for 16 hr. The reaction mixture was then neutralized with aqueous ammonium chloride and ethyl ether was added thereto. The organic layer was washed with water, dried over anhydrous magnesium sulfate, and filtered. The solvent was removed under reduced pressure and the resulting residue was purified by flash chromatography (eluent-ethyl acetate:hexane=1:4) to afford 3.99 g (yield 73%) of the title compound as a white solid.

M.p.: 124 to 125° C.; $^1$H-NMR (200 MHz, CDCl$_3$) δ 1.23 (3H, d, J=7.2 Hz), 1.38 (3H, d, J=7.2 Hz), 2.51 (3H, s), 3.34 (1H, m), 5.60 (1H, s), 7.57 (1H, s), 7.99 (1H, s), 8.07 (1H, s); m/z (EI) 365 (M$^+$).

Step 2) Synthesis of 2,4-Dimethoxy-5-isopropyl-6-(α-cyano-3'-nitro-5'-methylbenzyl)pyrimidine To a stirred anhydrous methanol solution (60 ml) of the compound obtained in Step 1) (3.65 g, 10 mmol), sodium methoxide (3.24 g, 60 mmol) was added at room temperature under a nitrogen atmosphere and refluxed for 24 hr. The reaction mixture was then allowed to cool to room temperature and neutralized with excess ammonium chloride. After removing the solvent, the resulting residue was purified by flash chromatography (eluent-ether:hexane=1:3) to afford 1.8 g (yield 50%) of the title compound as a light yellow solid.

M.p.: 134 to 135° C. $^1$H-NMR (200 MHz, CDCl$_3$) δ 1.15 (3H, d, J=6.7 Hz), 1.20 (3H, d, J=6.7 Hz), 2.49 (3H, s), 3.05 (1H, m), 4.00 (3H, s), 4.01 (3H, s), 5.48 (1H, s), 7.62 (1H, s), 8.00 (2H, s); m/z (EI) 356 (M$^+$).

Step 3) Synthesis of 2,4-Dimethoxy-5-isopropyl-6-(3'-nitro-5'-methylbenzoyl)pyrimidine To a stirred DMF solution (20 ml) of the compound obtained in Step 2) (1.7 g, 4.7 mmol), 60% sodium hydride dispersion (283 mg, 7.1 mmol) was added at room temperature under a nitrogen atmosphere. The mixture was then stirred in the presence of oxygen. After 5 hr, the reaction mixture was neutralized with ammonium chloride and ethyl ether was added thereto. The organic layer was washed with water, dried over anhydrous magnesium sulfate, and filtered. The solvent was removed under reduced pressure and the resulting residue was purified by flash chromatography (eluent-dichloromethane:hexane=97:3) to afford 1.039 (yield 62%) of the title compound as a white solid.

M.p.: 111 to 112° C.; $^1$H-NMR (200 MHz, CDCl$_3$) δ 1.21 (6H, d, J=6.9 Hz), 2.54 (3H, s), 2.88 (1H, m), 3.93 (3H, s), 4.09 (3H, s), 8.05 (1H, s), 8.27 (1H, s), 8.44 (1H, s); m/z (EI) 345 (M$^+$).

Step 4) Synthesis of 5-isopropyl-6-(3'-nitro-5'-methylbenzoyl)-2,4-pyrimidinedione The compound obtained in Step 3) (630 mg, 1.8 mmol) was refluxed with conc. hydrochloric acid (6 ml) for 4 hr and the reaction mixture was allowed to cool to room temperature. The precipitate was then collected, washed with distilled water and hexane, and dried to give 560 mg (yield 98%) of the title compound as a white solid.

TABLE 2

| Prep. No. | Comp. | Structure | M.p. (° C.) | $^1$H-NMR |
|---|---|---|---|---|
| 1 | (A) | 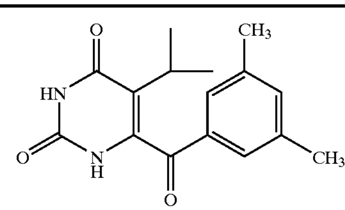 | 238–239 | (200 MHz, CDCl$_3$/CD$_3$OD) δ: 1.16(6H, d, J=6.9Hz), 2.35–2.49(7H, m), 7.35(2H, s), 7.53(2H, s). |
| 2 | (B) | 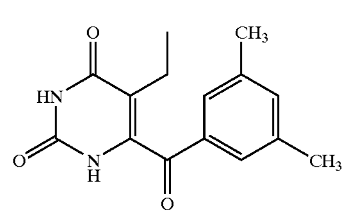 | 249–250 | (200 MHz, CDCl$_3$/CD$_3$OD) δ: 0.97(3H, t, J=7.4Hz), 2.17(2H, q, J=7.4Hz), 2.39(6H, s), 7.32(1H, s), 7.50(2H, s). |

TABLE 2-continued

| Prep. No. | Comp. | Structure | M.p. (° C.) | ¹H-NMR |
|---|---|---|---|---|
| 3 | (C) | 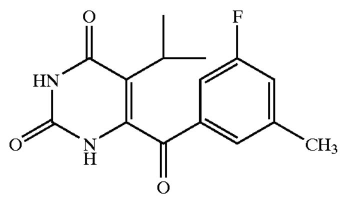 | 251–252 | (200 MHz, CD$_3$OD/DMSO-d$_6$) δ: 1.36(6H, d, J=6.9Hz), 2.38(1H, m), 2.46(3H, s), 7.26(1H, d, J=9.0Hz), 7.43(1H, d, J=8.4Hz), 7.52(1H, s). |
| 4 | (D) | 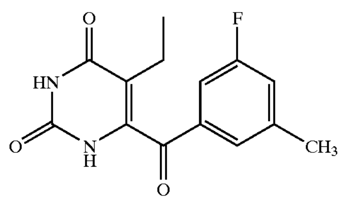 | 235–236 | (200 MHz, CD$_3$OD/DMSO-d$_6$) δ: 0.99(3H, t, J=7.4Hz), 2.17(2H, q, J=7.4Hz), 2.50(3H, s), 7.44(1H, d, J=9.4Hz), 7.59(1H, d, J=8.8Hz), 7.70(1H, m). |
| 5 | (E) | 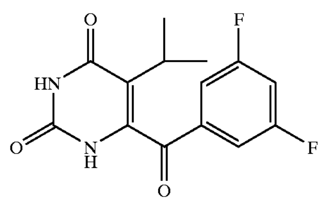 | 233–234 | (200 MHz, CDCl$_3$/CD$_3$OD) δ: 1.06(6H, d, J=7.0Hz), 2.32(1H, m), 7.07(1H, m), 7.25–7.38(2H, m). |
| 6 | (F) | 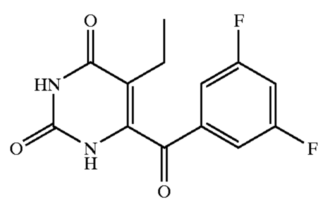 | 211–212 | (200 MHz, CDCl$_3$/CD$_3$OD) δ: 0.88(3H, t, J=7.3Hz), 2.06(2H, q, J=7.3Hz), 7.06(1H, m), 7.32–7.37(2H, m) |
| 7 | (G) | 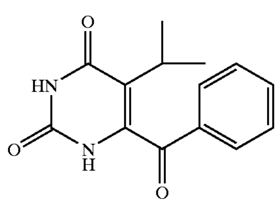 | 220–221 | (200 MHz, CD$_3$OD) δ: 1.16(6H, d, J=7.0Hz), 2.45(1H, m), 7.61–8.02(5H, m) |
| 8 | (H) | 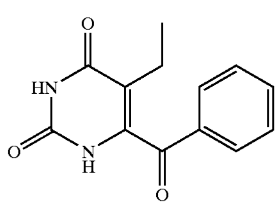 | 218–219 | (200 MHz, CD$_3$OD) δ: 0.98(3H, t, J=7.5Hz), 2.17(2H, q, J=7.5Hz), 7.58–8.03(5H, m) |
| 9 | (I) | 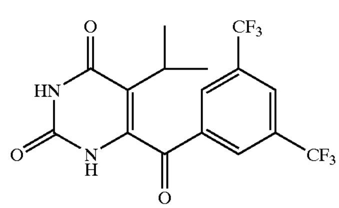 | 220–221 | (200 MHz, CDCl$_3$/CD$_3$OD) δ: 1.17(6H, d, J=6.8Hz), 2.39(1H, m), 8.21(1H, s), 8.37(2H, s). |

TABLE 2-continued

| Prep. No. | Comp. | Structure | M.p. (° C.) | ¹H-NMR |
|---|---|---|---|---|
| 10 | (J) | 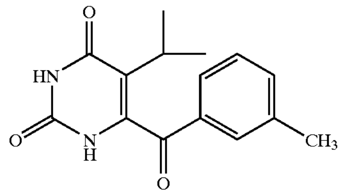 | 227–228 | (200 MHz, CDCl$_3$/CD$_3$OD) δ: 1.13(6H, d, J=7.0Hz), 2.35–2.50(4H, m), 7.42–7.72(4H, m), 9.82(1H, s). |
| 11 | (K) | 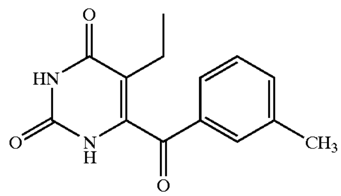 | 236–237 | (200 MHz, CDCl$_3$/CD$_3$OD) δ: 0.97(3H, t, J=7.5Hz), 2.18(2H, q, J=7.5Hz), 2.44(3H, s), 7.28–7.71(4H, m), 9.70(1H, s). |
| 12 | (L) | 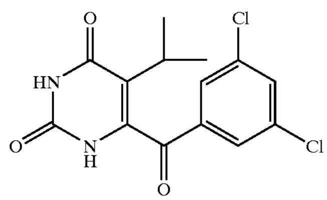 | 252–253 | (200 MHz, CDCl$_3$/CD$_3$OD) δ: 1.11(6H, d, J=6.9Hz), 2.33(1H, m), 7.61–7.73(3H, m). |
| 13 | (M) | 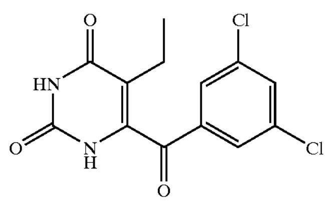 | 242–243 | (200 MHz, CDCl$_3$/CD$_3$OD) δ: 0.90(3H, t, J=7.5Hz), 2.07(2H, q, J=7.5Hz), 7.59(1H, t, J=1.8Hz), 7.67(2H, d, J=1.8Hz). |
| 14 | (N) | 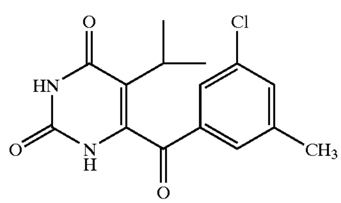 | 254–255 | (200 MHz, CDCl$_3$/CD$_3$OD) δ: 1.17(6H, d, J=6.9Hz), 2.25–2.45(4H, m), 7.50–7.71(3H, m). |
| 15 | (O) | 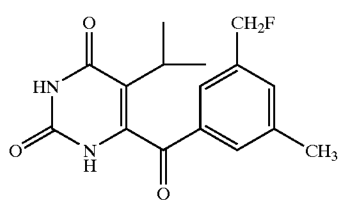 | 218–219 | (200 MHz, CDCl$_3$/CD$_3$OD) δ: 1.10(6H, d, J=6.9Hz), 2.32–2.52(4H, m), 5.41(2H, d, J=47.0Hz), 7.51–7.70(3H, m), 9.15(1H, s), 9.66(1H, s). |
| 16 | (P) | 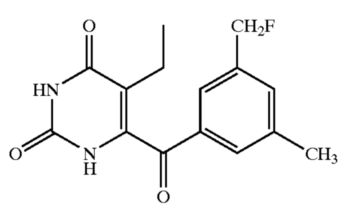 | 224–225 | (200 MHz, CDCl$_3$/CD$_3$OD) δ: 0.98(3H, t, J=7.4Hz), 2.16(2H, q, J=7.4Hz), 2.47(3H, s), 5.43(2H, d, J=47.2Hz), 7.54–7.71(3H, m). |

TABLE 2-continued

| Prep. No. | Comp. | Structure | M.p. (° C.) | ¹H-NMR |
|---|---|---|---|---|
| 17 | (Q) | 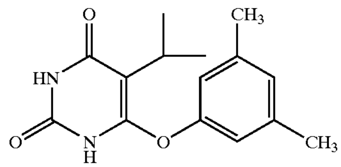 | 229–230 | (200 MHz, CD$_3$OD) δ: 1.20(6H, d, J=7.1Hz), 2.33(6H, s), 3.35(1H, m), 6.64(2H, s), 6.83(1H, s). |
| 18 | (R) | 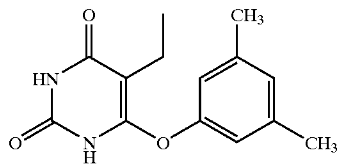 | 221–222 | (200 MHz, CD$_3$OD) δ: 0.90(3H, t, J=7.4Hz), 2.17–2.25(8H, m), 6.62(2H, s), 6.78(1H, s). |
| 19 | (S) | 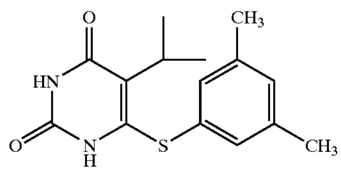 | 225–226 | (200 MHz, CDCl$_3$) δ: 1.34(6H, d, J=7.0Hz), 2.35(6H, s), 3.11(1H, m), 7.14(1H, s), 7.16(2H, s), 9.30(1H, s). |
| 20 | (T) | 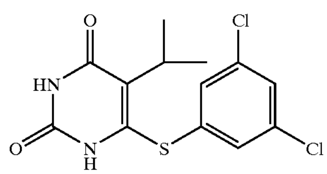 | 224–225 | (200 MHz, DMSO-d$_6$) δ: 1.17(6H, d, J=6.8Hz), 3.22(1H, m), 7.42(2H, s), 7.56(1H, s), 10.96(1H, s), 11.18(1H, s). |
| 21 | (U) | 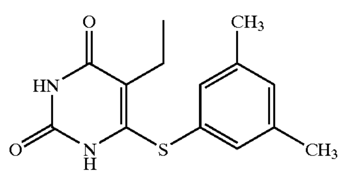 | 224–225 | (200 MHz, CDCl$_3$) δ: 1.14(3H, t, J=7.5Hz), 2.36(6H, s), 2.55(2H, q, J=7.5Hz), 7.06(1H, s), 7.16–7.26(3H, m), 9.04(1H, s) |
| 22 | (II-a-1) | 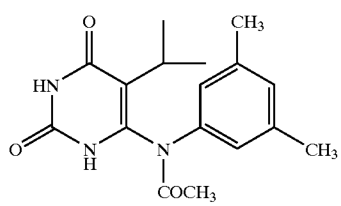 | 224–226 | (200 MHz, CDCl$_3$) δ: 1.12–1.33(6H, m), 2.02–2.15(3H, m), 2.31(6H, s), 2.90(1H, m), 6.99(3H, s) |
| 23 | (II-a-2) | 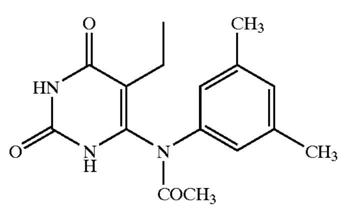 | 238–239 | (200 MHz, CDCl$_3$) δ: 0.93(3H, t, J=7.5Hz), 2.05–2.15(3H, m), 2.24–2.40(8H, m), 6.94–6.99(3H, m) |
| 24 | (II-b-1) | 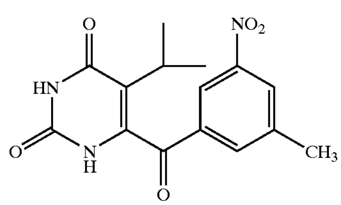 | 254–256 | (200 MHz, CDCl$_3$/CD$_3$OD) δ: 1.12(6H, d, J=7.0Hz), 2.40(1H, m), 2.54(3H, s), 8.11(1H, s), 8.37(1H, s), 8.49(1H, s) |

EXAMPLE 1

Synthesis of 1-(4'-Picolyl)-5-isopropyl-6-(3',5'-dimethylbenzoyl)-2,4-pyrimidinedione (Compound 1)

To a magnetically stirred DMF solution (5 ml) of compound (A) obtained in Preparation 1 (286 mg, 1 mmol) maintained at room temperature, were added anhydrous potassium carbonate (276 mg, 2 mmol), lithium iodide (134 mg, 1 mmol), and 4-picolyl chloride hydrochloride (164 mg, 1 mmol), in this order. After stirring for 16 hr, the solvent was removed under reduced pressure and the resulting residue was purified by flash chromatography (eluent-ethyl acetate:hexane=3:1) to afford 120 mg (yield 32%) of the title compound as a white solid.

M.p.: 264 to 265° C.; $^1$H-NMR (200 MHz; CDCl$_3$) δ 1.12 (3H, d, J=6.7 Hz), 1.23 (3H, d, J=6.7 Hz), 2.30–2.40 (7H, m), 4.66 (1H, d, J=16.3 Hz), 4.88 (1H, d, J=16.3 Hz), 6.98–7.36 (5H, m), 8.41–8.44 (2H, m), 9.91 (1H, s); m/z (EI) 377 (M$^+$).

EXAMPLE 2

Synthesis of 1-(3'-Picolyl)-5-isopropyl-6-(3', 5'-dimethylbenzoyl)-2,4-pyrimidinedione (Compound 2)

The procedure of Example 1 was repeated using 3-picolyl chloride hydrochloride in place of 4-picolyl chloride hydrochloride to prepare the title compound.

M.p.: 179 to 180° C.; $^1$H-NMR (200 MHz, CDCl$_3$) δ 1.12 (3H, d, J=6.9 Hz), 1.22 (3H, d, J=6.9 Hz), 2.20–2.38 (7H, m), 4.71 (1H, d, J=16.0 Hz), 4.93 (1H, d, J=16.0 Hz), 7.09–7.56 (5H, m), 8.29–8.43 (2H, m), 10.18 (1H, s); m/z (EI) 377 (M$^+$).

EXAMPLE 3

Synthesis of 1-(2'-Picolyl)-5-isopropyl-6-(3', 5'-dimethylbenzoyl)-2,4-pyrimidinedione (Compound 3)

The procedure of Example 1 was repeated using 2-picolyl chloride hydrochloride in place of 4-picolyl chloride hydrochloride to prepare the title compound.

M.p.: 214 to 215° C.; $^1$H-NMR (200 MHz, CDCl$_3$) δ 1.12 (3H, d, J=6.9 Hz), 1.23 (3H, d, J=6.9 Hz), 2.20–2.40 (7H, m), 4.77 (1H, d, J=16.8 Hz), 5.16 (1H, d, J=16.8 Hz), 7.01–7.48 (6H, m), 8.36 (2H, m), 9.90 (1H, s); m/z (EI) 377 (M$^+$).

EXAMPLES 4 to 65

The procedure of Example 1 was repeated to obtain the 2,4-pyrimidinedione derivatives of Examples 4–65 shown in Table 3.

TABLE 3

| Ex. No. | A | Z | R$^1$ | R$^2$ | R$^3$ | R$^4$ | $^1$H-NMR (200 MHz, CDCl$_3$) δ | M.p. (° C.) |
|---|---|---|---|---|---|---|---|---|
| 4 | O | C=O | 4-pyridyl | Ethyl | CH$_3$ | CH$_3$ | 0.97(3H, t, J=7.3Hz), 2.05(1H, m), 2.20–2.35(7H, m), 4.70(1H, d, J=16.4Hz), 4.90(1H, d, J=16.4Hz), 6.98–7.01(2H, m), 7.27(1H, s), 7.34(2H, s), 8.41–8.44 (2H, m), 9.25(1H, s). | 267–268 |
| 5 | O | C=O | 3-pyridyl | Ethyl | CH$_3$ | CH$_3$ | 0.95(3H, t, J=7.3Hz), 2.02(1H, s), 2.20–2.40(7H, m), 4.72(1H, d, J=16.4Hz), 4.90(1H, d, J=16.4Hz), 7.14(1H, s), 7.34(2H, s), 7.52(1H, m), 8.29–8.43(2H, m), 9.25(1H, s). | 197–198 |
| 6 | O | C=O | 2-pyridyl | Ethyl | CH$_3$ | CH$_3$ | 0.95(3H, t, J=7.1Hz), 2.05(1H, m), 2.20–2.40(7H, m), 4.81(1H, d, J=16.4Hz), 5.14(1H, d, J=16.4Hz), 7.01–7.52(6H, m), 8.40(1H, m), 9.11(1H, s). | 235–236 |
| 7 | O | C=O | 4-pyridyl | Isopropyl | CH$_3$ | F | 1.14(3H, d, J=6.7Hz), 1.23(3H, d, J=6.7Hz), 2.22–2.38(4H, m), 4.63(1H, d, J=16.3Hz), 4.94(1H, d, J=16.3Hz), 7.00–7.36(5H, m), 8.41–8.45(2H, m), 9.56(1H, s). | 207–209 |
| 8 | O | C=O | 3-pyridyl | Isopropyl | CH$_3$ | F | 1.12(3H, d, J=6.7Hz), 1.22(3H, d, J=6.7Hz), 2.27(1H, m), 2.34(3H, s), 4.64(1H, d, J=15.6Hz), 5.00(1H, d, J=16.4Hz), 7.10–7.53(5H, m), 8.27–8.42(2H, m), 9.41(1H, s). | 211–212 |
| 9 | O | C=O | 2-pyridyl | Isopropyl | CH$_3$ | F | 1.13(3H, d, J=6.9Hz), 1.22(3H, d, J=6.9Hz), 2.20–2.35(4H, m), 4.69(1H, d, J=16.4Hz), 5.29(1H, d, J=16.4Hz), 7.00–7.52(6H, m), 8.37(1H, m), 9.15(1H, s). | 187–189 |

TABLE 3-continued

| Ex. No. | A | Z | R¹ | R² | R³ | R⁴ | ¹H-NMR (200 MHz, CDCl₃) δ | M.p. (° C.) |
|---|---|---|---|---|---|---|---|---|
| 10 | O | C=O | 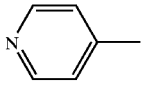 4-pyridyl | Ethyl | CH₃ | F | 0.98(3H, t, J=7.3Hz), 2.05(1H, m), 2.20–2.37(7H, m), 4.70(1H, d, J=16.4Hz), 4.92(1H, d, J=16.4Hz), 7.00–7.37(5H, m), 8.44–8.46(2H, m), 10.39(1H, s). | 233–234 |
| 11 | O | C=O | 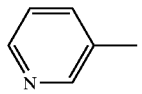 3-pyridyl | Ethyl | CH₃ | F | 0.95(3H, t, J=7.3Hz), 2.02(1H, m), 2.05(1H, m), 2.33(3H, s), 4.72(1H, d, J=16.4Hz), 5.02(1H, d, J=16.4Hz), 7.11–7.56(5H, m), 8.30–8.44(2H, m). | 189–190 |
| 12 | O | C=O | 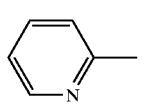 2-pyridyl | Ethyl | CH₃ | F | 0.96(3H, t, J=7.3Hz), 2.03(1H, m), 2.22(1H, m), 2.33(3H, s), 4.74(1H, d, J=16.4Hz), 5.23(1H, d, J=16.4Hz), 7.02–7.53(6H, m), 8.39(1H, m), 9.17(1H, s). | 158–159 |
| 13 | O | C=O | 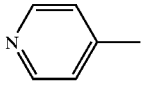 4-pyridyl | Isopropyl | F | F | 1.15(3H, d, J=7.0Hz), 1.23(3H, d, J=7.0Hz), 2.26(1H, m), 4.63(1H, d, J=16.2Hz), 4.94(1H, d, J=16.2Hz), 6.97–7.26(5H, m), 8.43–8.46(2H, m), 8.90(1H, s). | 189–190 |
| 14 | O | C=O | 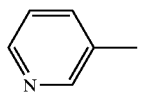 3-pyridyl | Isopropyl | F | F | 1.12(3H, d, J=6.7Hz), 1.21(3H, d, J=6.7Hz), 2.23(1H, m), 4.63(1H, d, J=15.8Hz), 5.06(1H, d, J=15.8Hz), 7.01–7.54(5H, m), 8.26(1H, m), 8.42(1H, m), 9.49(1H, s). | 227–230 |
| 15 | O | C=O | 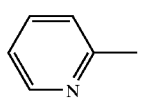 2-pyridyl | Isopropyl | F | F | 1.15(3H, d, J=6.9Hz), 1.22(3H, d, J=6.9Hz), 2.23(1H, m), 4.62(1H, d, J=16.6Hz), 5.31(1H, d, J=16.6Hz), 6.95–7.54(6H, m), 8.37(1H, m), 9.10(1H, s). | 214–215 |
| 16 | O | C=O | 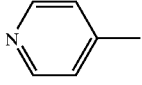 4-pyridyl | Ethyl | F | F | 0.97(3H, t, J=7.4Hz), 2.02(1H, m), 2.25(1H, m), 4.65–4.92(2H, m), 6.99–7.40(5H, m), 8.43–8.46(2H, m), 9.73(1H, s). | 223–224 |
| 17 | O | C=O | 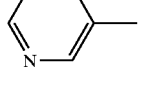 3-pyridyl | Ethyl | F | F | 0.96(3H, t, J=7.3Hz), 2.00(1H, m), 2.22(1H, m), 4.68(1H, m), 5.04(1H, m), 7.03–7.27(4H, m), 7.54(1H, m), 8.28–8.44(2H, m), 9.89(1H, s). | 217–218 |
| 18 | O | C=O | 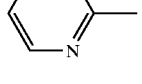 2-pyridyl | Ethyl | F | F | 0.97(3H, t, J=7.5Hz), 2.01(1H, m), 2.22(1H, m), 4.76(1H, m), 5.31(1H, m), 6.95–7.55(6H, m), 8.37(1H, m), 9.03(1H, s). | 206–207 |
| 19 | O | C=O | 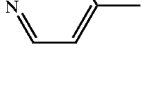 4-pyridyl | Isopropyl | Cl | Cl | 1.12(3H, d, J=6.9Hz), 1.25(3H, d, J=6.9Hz), 2.21(1H, m), 4.59(1H, d, J=16.6Hz), 4.99(1H, d, J=16.6Hz), 6.98(2H, d, J=5.9Hz), 7.55(3H, s), 8.44(2H, d, J=5.9Hz). | 232–233 |
| 20 | O | C=O | 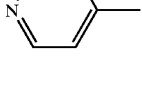 4-pyridyl | Ethyl | Cl | Cl | 0.98(3H, t, J=7.5Hz), 2.05(1H, m), 2.28(1H, m), 4.68(1H, d, J=16.5Hz), 5.02(1H, d, J=16.5Hz), 6.98(2H, d, J=5.9Hz), 7.54–7.74(3H, m), 8.45(2H, d, J=5.9Hz), 9.36(1H, s). | 243–245 |
| 21 | O | C=O | 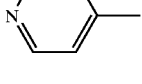 4-pyridyl | Isopropyl | CH₃ | Cl | 1.14(3H, d, J=6.7Hz), 1.23(3H, d, J=6.7Hz), 2.20–2.38(4H, m), 4.61(1H, d, J=16.3Hz), 4.95(1H, d, J=16.3Hz), 6.97–8.44(7H, m), 9.35(1H, s). | 248–249 |
| 22 | O | C=O | 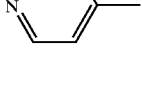 4-pyridyl | Isopropyl | CH₂F | CH₃ | 1.07(3H, d, J=6.7Hz), 1.18(3H, d, J=6.7Hz), 2.25(1H, m), 2.32(3H, s), 4.61(1H, d, J=16.4Hz), 4.84(1H, d, J=16.4Hz), 5.29(2H, d, J=47.2Hz), 6.97(2H, d, J=5.9Hz), 7.39–7.53(3H, m), 8.32(2H, d, J=5.9Hz). | 190 (dec.) |

TABLE 3-continued

| Ex. No. | A | Z | R¹ | R² | R³ | R⁴ | ¹H-NMR (200 MHz, CDCl₃) δ | M.p. (° C.) |
|---|---|---|---|---|---|---|---|---|
| 23 | O | C=O | 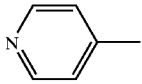 | Ethyl | CH₂F | CH₃ | 0.97(3H, t, J=7.5Hz), 2.04(1H, m), 2.25(1H, m), 2.36(3H, s), 4.68(1H, d, J=15.0Hz), 4.94(1H, d, J=15.0Hz), 5.33(2H, d, J=47.2Hz), 6.98–7.01(2H, m), 7.42–7.54(3H, m), 8.39–8.42(2H, m), 9.48(1H, s). | 227–228 |
| 24 | O | O | 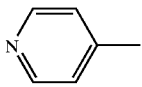 | Isopropyl | CH₃ | CH₃ | 1.14(6H, d, J=7.1Hz), 2.27(6H, s), 2.84(1H, m), 4.88(2H, s), 6.44(2H, s), 6.75(1H, s), 7.11(2H, dd, J=4.5Hz, J=1.6Hz), 8.54(2H, dd, J=4.5Hz, J=1.6Hz), 9.79(1H, s). | 213–215 |
| 25 | O | O | 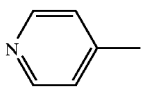 | Ethyl | CH₃ | CH₃ | 0.94(3H, t, J=7.5Hz), 2.21(2H, q, J=7.5Hz), 2.27(6H, s), 4.92(2H, s), 6.45(2H, s), 6.76(1H, s), 7.13(2H, d, J=6.1Hz), 8.54(2H, d, J=6.1Hz), 8.95(1H, s). | 229–230 |
| 26 | O | S | 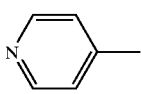 | Isopropyl | Cl | Cl | 1.21(6H, d, J=6.9Hz), 3.33(1H, m), 5.20(2H, s), 6.81–7.11(5H, m), 8.43–8.46(2H, m), 9.70(1H, s). | 198–199 |
| 27 | O | S | 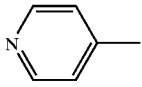 | Isopropyl | CH₃ | CH₃ | 1.26(6H, d, J=6.9Hz), 2.21(6H, s), 3.52(1H, m), 5.25(2H, s), 6.65(2H, s), 6.80(1H, s, 7.01(2H, d, J=5.7Hz), 8.50(2H, d, J=5.7Hz), 10.82(1H, s). | 186–187 |
| 28 | O | S | 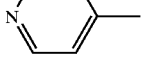 | Ethyl | CH₃ | CH₃ | 1.07(3H, t, J=7.5Hz), 2.23(6H, s), 2.73(2H, q, J=7.5Hz), 5.21(2H, s), 6.68(2H, s), 6.82(1H, s), 6.98(2H, d, J=6.3Hz), 8.48(2H, d, J=6.3Hz), 8.97(1H, s). | 191–192 |
| 29 | O | C=O | 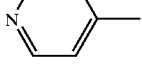 | Isopropyl | CF₃ | CF₃ | 1.14(3H, d, J=6.9Hz), 1.24(3H, d, J=6.9Hz), 2.18(1H, m), 4.51(1H, d, J=16.3Hz), 5.28(1H, d, J=16.3Hz), 6.95(2H, d, J=6.1Hz), 8.07(1H, s), 8.11(2H, s), 8.37(2H, d, J=6.1Hz). | 236–237 |
| 30 | O | C=O | 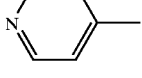 | Ethyl | CF₃ | CF₃ | 0.97(3H, t, J=7.3Hz), 2.00–2.35(2H, m), 4.60(1H, m), 5.22(1H, m), 6.94–6.98(2H, m), 8.07(3H, s), 8.35–8.38(2H, m), 9.73(1H, s). | 208–209 |
| 31 | O | C=O | 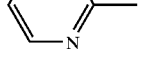 | Isopropyl | CF₃ | CF₃ | 1.14(3H, t, J=6.7Hz), 1.23(3H, d, J=6.7Hz), 2.16(1H, m), 4.51(1H, d, J=16.4Hz), 5.51(1H, d, J=16.4Hz), 6.94–7.49(3H, m), 8.03–8.32(4H, m), 9.61(1H, s). | 185–186 |
| 32 | O | C=O | 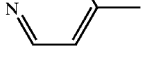 | Isopropyl | CH₃ | H | 1.12(3H, d, J=6.7Hz), 1.22(3H, d, J=6.7Hz), 2.26–2.36(4H, m), 4.65(1H, d, J=16.0Hz), 4.86(1H, d, J=16.0Hz), 6.97(2H, d, J=5.9Hz), 7.25–7.60(4H, m), 8.38(2H, d, J=5.9Hz). | 226–227 |
| 33 | O | C=O | 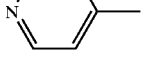 | Ethyl | CH₃ | H | 0.97(3H, t, J=7.4Hz), 2.06(1H, m), 2.26(1H, m), 2.34(3H, s), 4.72(1H, d, J=16.0Hz), 4.84(1H, d, J=16.0Hz), 6.99–7.02(2H, m), 7.29–7.62(4H, m), 8.41–8.44(2H, m), 9.93(1H, s). | 218–219 |
| 34 | O | C=O | 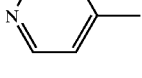 | Isopropyl | H | H | 1.15(3H, d, J=6.9Hz), 1.25(3H, d, J=6.9Hz), 2.34(1H, m), 4.70(1H, d, J=16.4Hz), 4.87(1H, d, J=16.4Hz), 6.99–7.82(7H, m), 8.40–8.44(2H, m), 10.16(1H, s). | 238–239 |
| 35 | O | C=O | 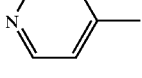 | Ethyl | H | H | 0.97(3H, t, J=7.4Hz), 2.05(1H, m), 2.24(1H, m), 4.65–4.94(2H, m), 6.99–7.80(7H, m), 8.40–8.44(2H, m), 9.68(1H, s). | 219–220 |

TABLE 3-continued

| Ex. No. | A | Z | R¹ | R² | R³ | R⁴ | ¹H-NMR (200 MHz, CDCl₃) δ | M.p. (° C.) |
|---|---|---|---|---|---|---|---|---|
| 36 | O | C=O | phenyl | Isopropyl | CH₃ | CH₃ | 1.08(3H, d, J=6.9Hz), 1.21(3H, d, J=6.9Hz), 2.20–2.40(7H, m), 4.59(1H, d, J=15.6Hz), 5.07(1H, d, J=15.6Hz), 7.02–7.12(5H, m), 7.18(1H, s), 7.26(2H, s), 8.85(1H, s). | 199–200 |
| 37 | O | C=O | phenyl | Ethyl | CH₃ | CH₃ | 0.93(3H, t, J=7.3Hz), 2.02(1H, m), 2.12–2.28(7H, m), 4.64(1H, d, J=15.6Hz), 5.07(1H, d, J=15.6Hz), 7.02–7.26(8H, m), 8.97(1H, s). | 221–222 |
| 38 | O | C=O | 4-O₂N-phenyl | Isopropyl | CH₃ | CH₃ | 1.12(3H, d, J=6.9Hz), 1.22(3H, d, J=6.9Hz), 2.20–2.40(7H, m), 4.77(1H, d, J=16.0Hz), 4.98(1H, d, J=16.0Hz), 7.23–7.32(5H, m), 8.00(2H, d, J=8.5Hz), 8.97(1H, s). | 203–204 |
| 39 | O | C=O | 4-H₃CO-phenyl | Isopropyl | CH₃ | CH₃ | 1.07(3H, d, J=6.9Hz), 1.20(3H, d, J=6.9Hz), 2.20–2.40(7H, m), 3.69(3H, s), 4.50(1H, d, J=15.2Hz), 5.07(1H, d, J=15.2Hz), 6.57–7.31(7H, m), 8.74(1H, s). | 156–157 |
| 40 | O | C=O | 3,5-(H₃C)₂-4-Cl-phenyl | Isopropyl | CH₃ | CH₃ | 1.10(3H, d, J=6.7Hz), 1.21(3H, d, J=6.7Hz), 2.11(3H, s), 2.25–2.38(7H, m), 4.34(1H, d, J=15.8Hz), 5.23(1H, d, J=15.8Hz), 6.66(1H, s), 6.77(1H, s), 6.83(1H, s), 7.19(1H, s), 7.27(2H, s), 8.72(1H, s). | 226–227 |
| 41 | O | C=O | 4-O₂N-phenyl | Ethyl | CH₃ | CH₃ | 0.96(3H, t, J=7.5Hz), 2.08(1H, m), 2.20–2.40(7H, m), 4.84(1H, d, J=16.6Hz), 5.00(1H, d, J=16.6Hz), 7.25–7.32(5H, m), 7.98–8.05(2H, m), 9.43(1H, s). | 230–231 |
| 42 | O | C=O | 4-H₃CO-phenyl | Ethyl | CH₃ | CH₃ | 0.92(3H, t, J=7.3Hz), 2.05(1H, m), 2.10–2.40(7H, m), 3.69(3H, s), 4.56(1H, d, J=15.4Hz), 5.07(1H, d, J=15.4Hz), 6.59–7.26(7H, m), 9.25(1H, s). | 157–158 |
| 43 | O | C=O | 3,5-F₂-phenyl | Isopropyl | CH₃ | CH₃ | 1.12(3H, d, J=6.9Hz), 1.22(3H, d, J=6.9Hz), 2.22–2.40(7H, m), 4.54(1H, d, J=16.3Hz), 4.99(1H, d, J=16.3Hz), 6.50–6.60(3H, m), 7.24(1H, s), 7.35(2H, s), 9.25(1H, s). | 208–209 |
| 44 | O | C=O | 3,5-(F₃C)₂-phenyl | Isopropyl | CH₃ | CH₃ | 1.12(3H, d, J=6.9Hz), 1.23(3H, d, J=6.9Hz), 2.25(6H, s), 2.30(1H, m), 4.62(1H, d, J=15.9Hz), 5.33(1H, d, J=15.9Hz), 7.19–7.30(3H, m), 7.51(2H, s), 7.58(1H, s), 9.92(1H, s). | 184–185 |
| 45 | O | C=O | 2-H₃C-pyridin-5-yl | Isopropyl | CH₃ | CH₃ | 1.05(3H, d, J=6.7Hz), 1.15(3H, d, J=6.7Hz), 2.22–2.32(10H, m), 4.44(1H, d, J=16.0Hz), 4.90(1H, d, J=16.0Hz), 6.69–6.72(2H, m), 7.16(1H, s), 7.19(2H, s), 8.20(1H, d, J=5.5Hz), 8.82(1H, s). | 269–270 |
| 46 | O | C=O | 2-H₃C-pyridin-5-yl | Isopropyl | CH₃ | F | 1.15(3H, d, J=7.0Hz), 1.20(3H, d, J=7.0Hz), 2.21(1H, m), 2.24(3H, s), 2.34(3H, s), 4.42(1H, d, J=16.2Hz), 4.96(1H, d, J=16.2Hz), 6.70–7.26(5H, m), 8.21(1H, d, J=5.9Hz), 9.25(1H, s). | 217–218 |

TABLE 3-continued

| Ex. No. | A | Z | R¹ | R² | R³ | R⁴ | ¹H-NMR (200 MHz, CDCl₃) δ | M.p. (° C.) |
|---|---|---|---|---|---|---|---|---|
| 47 | O | C=O | 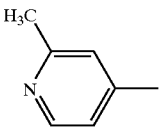 | Isopropyl | CH₃ | Cl | 1.14(3H, d, J=6.7Hz), 1.22(3H, d, J=6.7Hz), 2.22–2.38(4H, m), 2.41(3H, s), 4.46(1H, d, J=16.2Hz), 5.07(1H, d, J=16.2Hz), 6.77–8.30(6H, m), 9.50(1H, s). | 253–254 |
| 48 | O | C=O | 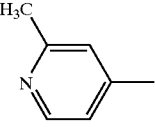 | Isopropyl | Cl | Cl | 1.15(3H, d, J=6.9Hz), 1.23(3H, d, J=6.9Hz), 2.23(1H, m), 2.44(3H, s), 4.41(1H, d, J=16.2Hz), 5.18(1H, d, J=16.2Hz), 6.75–8.30(6H, m), 9.42(1H, s). | 234–236 |
| 49 | O | C=O | 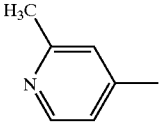 | Isopropyl | CH₂F | CH₃ | 1.12(3H, d, J=6.7Hz), 1.22(3H, d, J=6.7Hz), 2.26–2.37(7H, m), 4.48(1H, d, J=16.5Hz), 5.04(1H, d, J=16.5Hz), 5.31(2H, d, J=47.2Hz), 6.75–6.78(2H, m), 7.39–7.52(3H, m), 8.24(1H, m), 8.85(1H, s). | 253–255 |
| 50 | O | C=O | 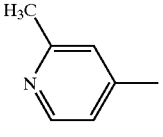 | Isopropyl | CH₃ | H | 1.13(3H, d, J=7.0Hz), 1.23(3H, d, J=7.0Hz), 2.24–2.39(7H, m), 4.54(1H, d, J=16.1Hz), 4.95(1H, d, J=16.1Hz), 6.77–8.28(7H, m), 8.96(1H, s). | 219–220 |
| 51 | O | C=O | 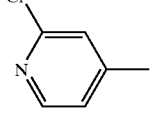 | Isopropyl | CH₃ | CH₃ | 1.15(3H, d, J=6.7Hz), 1.24(3H, d, J=6.7Hz), 2.28–2.42(7H, m), 4.55(1H, d, J=16.4Hz), 4.97(1H, d, J=16.4Hz), 6.94–6.96(2H, m), 7.26(1H, s), 7.35(2H, s), 8.18(1H, m), 9.29(1H, s). | 253–254 |
| 52 | O | C=O | 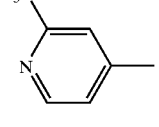 | Ethyl | CH₃ | CH₃ | 0.96(3H, t, J=7.5Hz), 2.05(1H, m), 2.20–2.30(7H, m), 2.40(3H, s), 4.57(1H, d, J=16.3Hz), 4.96(1H, d, J=16.3Hz), 6.79–6.82(2H, m), 7.24(1H, s), 7.31(2H, s), 8.29(1H, d, J=4.6Hz), 9.55(1H, s). | 211–212 |
| 53 | O | C=O | 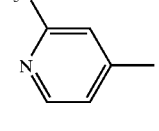 | Ethyl | CH₃ | F | 0.97(3H, t, J=7.4Hz), 2.02(1H, m), 2.22–2.31(4H, m), 2.42(3H, s), 4.56(1H, d, J=16.8Hz), 5.02(1H, d, J=16.8Hz), 6.79–7.33(5H, m), 8.30(1H, m), 9.64(1H, s). | 183–184 |
| 54 | O | C=O | 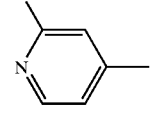 | Ethyl | CH₃ | CH₃ | 0.98(3H, t, J=7.5Hz), 2.10(1H, m), 2.25–2.32(7H, m), 4.59(1H, d, J=15.6Hz), 4.96(1H, d, J=15.6Hz), 6.94–6.97(2H, m), 7.27(1H, s), 7.33(2H, s), 8.19(1H, m), 9.34(1H, s). | 217–218 |
| 55 | O | C=O | 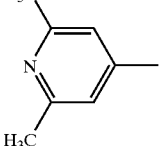 | Isopropyl | CH₃ | CH₃ | 1.11(3H, d, J=6.7Hz), 1.21(3H, d, J=6.7Hz), 2.22–2.38(13H, m), 4.37(1H, d, J=16.0Hz), 5.05(1H, d, J=16.0Hz), 6.56(2H, s), 7.19(1H, s), 7.27(2H, s), 9.70(1H, s). | 232–233 |
| 56 | O | C=O | 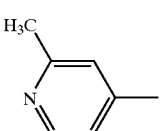 | Isopropyl | F | F | 1.15(3H, d, J=6.7Hz), 1.22(3H, d, J=6.7Hz), 2.23(1H, m), 2.36(6H, s), 4.34(1H, d, J=16.2Hz), 5.18(1H, d, J=16.2Hz), 6.58(2H, s), 7.01–7.20(3H, m), 9.25(1H, s). | 176–178 |

TABLE 3-continued

| Ex. No. | A | Z | R¹ | R² | R³ | R⁴ | ¹H-NMR (200 MHz, CDCl₃) δ | M.p. (° C.) |
|---|---|---|---|---|---|---|---|---|
| 57 | O | C=O | 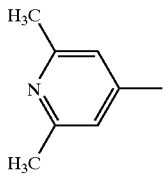 | Isopropyl | Cl | Cl | 1.13(3H, d, J=6.9Hz), 1.23(3H, d, J=6.9Hz), 2.20(1H, m), 2.35(6H, s), 4.22(1H, d, J=16.3Hz), 5.30(1H, d, J=16.3Hz), 6.54(2H, s), 7.46(2H, s), 7.50(1H, s), 9.35(1H, s). | 172–173 (foam) |
| 58 | O | C=O | 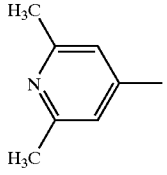 | Isopropyl | CH₂F | CH₃ | 1.12(3H, d, J=6.7Hz), 1.22(3H, d, J=6.7Hz), 2.22–2.35(10H, m), 4.35(1H, d, J=16.0Hz), 5.13(1H, d, J=16.0Hz), 5.31(2H, d, J=47.2Hz), 6.56(2H, s), 7.37–7.50(3H, m), 9.06(1H, s). | 197–198 (foam) |
| 59 | O | C=O | 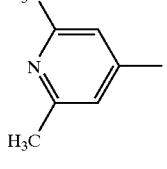 | Isopropyl | Cl | CH₃ | 1.13(3H, d, J=6.7Hz), 1.23(3H, d, J=6.7Hz), 2.20–2.35(10H, m), 4.32(1H, d, J=16.0Hz), 5.19(1H, d, J=16.0Hz), 6.56(2H, s), 7.27–7.50(3H, m), 9.34(1H, s). | 222–223 |
| 60 | O | C=O | 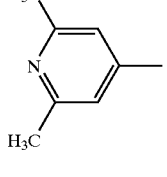 | Ethyl | CH₃ | CH₃ | 0.95(3H, t, J=7.5Hz), 2.02(1H, m), 2.20–2.33(13H, m), 4.45(1H, d, J=16.0Hz), 5.05(1H, d, J=16.0Hz), 6.59(2H, s), 7.22(1H, s), 7.29(2H, s), 9.45(1H, s). | 211–212 |
| 61 | O | C=O | 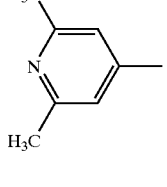 | Ethyl | F | F | 1.15(3H, d, J=6.7Hz), 1.22(3H, d, J=6.7Hz), 2.23(1H, m), 2.36(6H, s), 4.34(1H, d, J=16.2Hz), 5.18(1H, d, J=16.2Hz), 6.58(2H, s), 7.01–7.20(3H, m), 9.25(1H, s). | 176–178 |
| 62 | O | C=O | 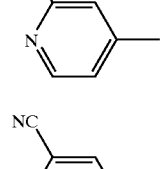 | Isopropyl | CH₃ | CH₃ | 1.14(3H, d, J=6.7Hz), 1.23(3H, d, J=6.7Hz), 2.30–2.40(7H, m), 4.69(1H, d, J=16.4Hz), 4.86(1H, d, J=16.4Hz), 7.27–7.37(5H, m), 8.52(1H, m), 9.50(1H, s). | 236–238 |
| 63 | O | C=O | 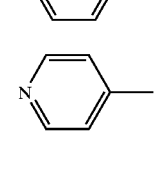 | Isopropyl | CH₃ | Cl | 1.16(3H, d, J=6.7Hz), 1.22(3H, d, J=6.7Hz), 2.30(1H, m), 2.40(3H, s), 4.77(2H, s), 7.27–7.56(5H, m), 8.56(1H, d, J=5.1Hz), 9.27(1H, s). | 220–221 |
| 64 | O | C=O | 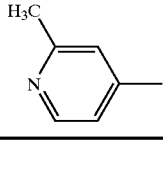 | Isopropyl | CH₃ | NO₂ | (CDCl₃/CD₃OD) δ 1.11(3H, d, J=7.1Hz), 1.23(3H, d, J=7.1Hz), 2.23(1H, m), 2.49(3H, s), 4.63(1H, d, J=16.2Hz), 4.98(1H, d, J=16.2Hz), 7.02(2H, d, J=5.7Hz), 7.84(1H, s), 8.27–8.35(4H, m). | 256–257 |
| 65 | O | C=O |  | Isopropyl | CH₃ | NO₂ | 1.13(3H, d, J=6.7Hz), 1.23(3H, d, J=6.7Hz), 2.22(1H, m), 2.37(3H, s), 2.46(3H, s), 4.41(1H, d, J=16.2Hz), 5.25(1H, d, J=16.2Hz), 6.75–6.79(2H, m), 7.76(1H, s), 8.21–8.28(3H, m), 9.76(1H, s). | 237–238 |

EXAMPLE 66

Synthesis of 1-(4'-Picolyl)-5-isopropyl-6-(3', 5'-dimethylphenylamino)-2,4-pyrimidinedione (Compound 66)

To a magnetically stirred DMF solution (10 ml) of compound (II-a-1) obtained in Preparation 22 (630 mg, 2 mmol) at room temperature, were added anhydrous potassium carbonate (552 mg, 4 mmol), lithium iodide (268 mg, 2 mmol), and 4-picolyl chloride hydrochloride (328 mg, 2 mmol). After stirring for 24 hr, the solvent was removed under reduced pressure and the resulting residue was purified by flash chromatography (eluent-ethyl acetate) to give 276 mg (yield 34%) of 1-(4'-picolyl)-5-isopropyl-6-(3', 5'-dimethylphenylacetamido)-2,4-pyrimidinedione. The compound thus obtained was then refluxed in methanol (10 ml) with sodium methoxide (110 mg, 2 mmol) for 6 hr. The reaction mixture was allowed to cool to room temperature and neutralized with excess ammonium chloride. The solvent was removed under reduced pressure and the resulting residue was purified by flash chromatography (eluent-methanol:ether=8:92) to afford 280 mg (yield 88%) of the title compound as a white solid.

M.p.: 272 to 273° C.; $^1$H-NMR (200 MHz, CDCl$_3$) δ 1.20 (6H, d, J=6.9 Hz), 2.24 (6H, s), 2.90 (1H, m), 4.90 (2H, s), 6.27 (2H, s), 6.61 (1H, s), 7.04–7.06 (2H, m), 8.42–8.45 (2H, m); m/z (EI) 364 (M$^+$).

EXAMPLE 67

Synthesis of 1-(4'-Picolyl)-5-ethyl-6-(3', 5'-dimethylphenylamino)-2,4-pyrimidinedione (Compound 67)

The procedure of Example 66 was repeated using compound (II-a-2) obtained in Preparation 23 in place of compound (II-a-1) to prepare the title compound.

M.p.: 250 to 251° C.; $^1$H-NMR (200 MHz, CDCl$_3$/CD$_3$OD) δ 0.99 (3H, t, J=7.5 Hz), 2.24 (6H, s), 2.37 (2H, q, J=7.5 Hz), 4.91 (2H, s), 6.31 (2H, s), 6.62 (1H, s), 7.04–7.07 (2H, m), 8.40–8.43 (2H, m); m/z (EI) 350 (M$^+$).

EXAMPLE 68

Synthesis of 1-(N-oxo-4'-Picolyl)-5-isopropyl-6-(3', 5'-dimethylbenzoyl)-2,4-pyrimidinedione (Compound 68)

Compound 1 obtained in Example 1 (2.26 g, 6 mmol) was stirred with m-chloroperbenzoic acid (2.72 g, 9 mmol) in dichloromethane (120 ml) at room temperature. After 6 hr, the solvent was removed and the residue was purified by flash chromatography (eluent-chloroform:methanol=93:7) to afford 2 g (yield 84%) of the title compound as a white solid.

M.p.: 254 to 255° C.; $^1$H-NMR (200 MHz, CDCl$_3$) δ 1.12 (3H, d, J=6.7 Hz), 1.22 (3H, d, J=6.7 Hz), 2.25–2.36 (7H, m), 4.69 (2H, s), 7.05–7.41 (5H, m), 8.05–8.09 (2H, m), 9.52 (1H, s); m/z (EI) 393 (M$^+$).

EXAMPLE 69

Synthesis of 1-(N-oxo-3'-Methyl-4'-picolyl)-5-isopropyl-6-(3', 5'-dimethylbenzoyl)-2,4-pyrimidinedione (Compound 69)

Compound 45 obtained in Example 45 (834 mg, 2.13 mmol) was stirred with m-chloroperbenzoic acid (969 mg, 3.2 mmol) in dichloromethane (40 ml) at room temperature. After 5 hr, the solvent was removed and the residue was purified by flash chromatography (eluent-ethyl acetate:methanol=7:1) to afford 860 mg (yield 99%) of the title compound as a white solid.

M.p.: 223 to 224° C.; $^1$H-NMR (200 MHz, CDCl$_3$) δ 1.13 (3H, d, J=6.7 Hz), 1.23 (3H, d, J=6.7 Hz), 2.25–2.40 (10H, m), 4.56 (1H, d, J=16.0 Hz), 4.85 (1H, d, J=16.0 Hz), 6.93 (1H, m), 7.31 (1H, s), 7.37 (2H, s), 8.10 (1H, m), 10.08 (1H, s); m/z (EI) 407 (M$^+$).

EXAMPLE 70

Synthesis of 1-(N-oxo-3', 5-Dimethyl-4'-picolyl)-5-Isopropyl-6-(3', 5'-dimethylbenzoyl)-2,4-Pyrimidinedione (Compound 70)

Compound 55 obtained in Example 55 (840 mg, 2 mmol) was stirred with m-chloroperbenzoic acid (942 mg, 3 mmol) in dichloromethane (40 ml) at room temperature. After 20 hr, the solvent was removed and the residue was purified by flash chromatography (eluent-dichloromethane:methanol=15:1) to afford 800 mg (yield 95%) of the title compound as a white solid.

M.p.: 241 to 242° C.; $^1$H-NMR (200 MHz, CDCl$_3$) δ 1.12 (3H, d, J=6.7 Hz), 1.22 (3H, d, J=6.7 Hz), 2.30–2.34 (13H, m), 4.41 (1H, d, J=16.0 Hz), 54.98 (1H, d, J=16.0 Hz), 6.80 (2H, s), 7.27 (1H, m), 7.34 (2H, s), 9.21 (1H, s); m/z (EI) 421 (M$^+$).

EXAMPLE 71

Synthesis of 1-(N-oxo-3',5'-Dimethyl-4'-picolyl)-5-isopropyl-6-(3',-chloro-5-methylbenzoyl)-2,4-pyrimidinedione (Compound 71)

Compound 59 obtained in Example 59 (860 mg, 2 mmol) was stirred with m-chloroperbenzoic acid (942 mg, 3 mmol) in dichloromethane (40 ml) at room temperature. After 21 hr, the solvent was removed and the residue was purified by flash chromatography (eluent-ethyl acetate:hexane=10:1) to afford 870 mg (yield 98%) of the title compound as a white solid.

M.p.: 2 to 226° C.; $^1$H-NMR (200 MHz, CDCl$_3$) δ 1.13 (3H, d, J=6.9 Hz), 1.22 (3H, d, J=6.9 Hz), 2.22–2.36 (13H, m), 4.39 (1H, d, J=16.0 Hz), 5.04 (1H, d, J=16.0 Hz), 6.80 (2H, s), 7.33–7.54 (3H, m), 9.14 (1H, s); m/z (EI) 441 (M$^+$).

EXAMPLE 72

Synthesis of 1-(3'-Acetoxymethyl-4'-picolyl)-5-Isopropyl-6-(3',5'-dimethylbenzoyl)-2,4-pyrimidinedione (Compound 72)

Compound 69 obtained in Example 69 (800 mg, 1.96 mmol) was dissolved in acetic anhydride (10 ml) and the solution was heated in an oil bath (120–140° C.) with stirring for 4 hr. The solvent was then removed under reduced pressure and the residue was purified by flash chromatography (eluent-ethyl acetate:hexane=2:1) to afford 150 mg (yield 17%) of the title compound as a syrup.

$^1$H-NMR (200 MHz, CDCl$_3$) δ 1.14 (3H, d, J=6.7 Hz), 1.28 (3H, d, J=6.7 Hz), 2.16 (3H, s), 2.22–2.40 (7H, m), 4.68 (1H, d, J=16.2 Hz), 4.88 (1H, d, J=16.2 Hz), 5.08 (2H, s), 7.00–7.02 (2H, m), 7.26 (1H, s), 7.36 (2H, s), 8.44 (1H, m); m/z (EI) 449 (M$^+$).

EXAMPLE 73

Synthesis of 1-(3'-Acetoxymethyl-5'-methyl-4'-picolyl)-5-isopropyl-6-(3',5'-dimethylbenzoyl)-2,4-pyrimidinedione (Compound 73)

Compound 70 obtained in Example 70 (300 mg, 0.71 mmol) was dissolved in acetic anhydride (3 ml) and the solution was heated in an oil bath (120–130° C.) with stirring for 2 hr. The solvent was then removed under reduced pressure and the residue was purified by flash chromatography (eluent-ethyl acetate:hexane=1:1) to afford 110 mg (yield 33%) of the title compound as a foam.

$^1$H-NMR (200 MHz, CDCl$_3$) δ 1.13 (3H, d, J=6.9 Hz), 1.23 (3H, d, J=6.9 Hz), 2.10–2.41 (10H, m), 4.53 (1H, d, J=16.0 Hz), 4.96 (1H, d, J=16.0 Hz), 5.00 (2H, s), 6.78–6.81 (2H, m), 7.24 (1H, s), 7.34 (2H, s); m/z (EI) 463 (M$^+$).

EXAMPLE 74

Synthesis of 1-(3'-Acetoxymethyl -5'-methyl-4-picolyl)-5-isopropyl-6-(3'-chloro-5'-methylbenzoyl)-2,4-pyrimidinedione (Compound 74)

Compound 71 obtained in Example 71 (700 mg, 1.58 mmol) was dissolved in acetic anhydride (10 ml) and the solution was heated in an oil bath (120–130° C.) with stirring for 5 hr. The solvent was then removed under reduced pressure and the residue was purified by flash chromatography (eluent-ethyl acetate:hexane=2:1) to afford 115 mg (yield 15%) of the title compound as a foam.

$^1$H-NMR (200 MHz, CDCl$_3$) δ 1.14 (3H, d, J=6.9 Hz), 1.24 (3H, d, J=6.9 Hz), 2.16 (3H, s), 2.20–2.32 (4H, m), 2.42 (3H, s), 4.48 (1H, d, J=16.3 Hz), 5.00 (2H, s), 5.06 (1H, d, J=16.3 Hz), 6.76 (2H, d, J=5.9 Hz), 7.32 (1H, s), 7.39 (1H, s), 7.52 (1H, s), 9.46 (1H, s); m/z (EI) 483 (M$^+$).

EXAMPLE 75

Synthesis of 1-(3'-Hydroxymethyl-4'-picolyl)-5-isopropyl-6-(3',5'-dimethylbenzoyl)-2,4-pyrimidinedione (Compound 75)

Compound 72 obtained in Example 72 (100 mg, 0.22 mmol) was stirred with ammonium hydroxide (0.5 ml) in methanol (5 ml) at room temperature. After 6 hr, the solvent was evaporated in vacuo and the resulting residue was recrystallized from methanol-chloroform to give 70 mg (yield 77%) of the title compound as a white solid.

M.p.: 256 to 257° C.; $^1$H-NMR (200 MHZ, DMSO-d$_6$) δ 1.05 (3H, d, J=6.8 Hz), 1.11 (3H, d, J=6.8 Hz), 2.15 (1H, m), 2.28 (6H, s), 4.44 (2H, d, J=5.5 Hz), 4.59 (1H, d, J=16.7 Hz), 4.70 (1H, d, J=16.7 Hz), 5.35 (1H, t, J=5.5 Hz), 6.90 (1H, m), 7.15 (1H, s), 7.32 (1H, s), 7.55 (2H, s), 8.25 (1H, s), 11.66 (1H, s); m/z (EI) 407 (M$^+$).

EXAMPLE 76

Synthesis of 1-(3'-Hydroxymethyl-5'-methyl-4'-picolyl)-5-isopropyl-6-(3', 5'-dimethylbenzoyl)-2,4-pyrimidinedione (Compound 76)

Compound 73 obtained in Example 73 (150 mg, 0.32 mmol) was stirred with ammonium hydroxide (0.5 ml) in methanol (5 ml) at room temperature. After 5 hr, the solvent was evaporated in vacuo and the resulting residue was recrystalized from methanol-chloroform to give 100 mg (yield 74%) of the title compound as a white solid.

M.p.: 234 to 236° C.; $^1$H-NMR (200 MHZ, DMSO-d$_6$) δ 1.05 (3H, d, J=6.7 Hz), 1.11 (3H, d, J=6.7 Hz), 2.15 (1H, m), 2.26 (9H, s), 4.37 (2H, d, J=5.3 Hz), 4.51 (1H, d, J=17.1 Hz), 4.72 (1H, d, J=17.1 Hz), 5.29 (1H, t, J=5.3 Hz), 6.72 (1H, s), 6.93 (1H, s), 7.30 (1H, s), 7.51 (2H, s), 11.64 (1H, s); m/z (EI) 421 (M$^+$).

EXAMPLE 77

Synthesis of 1-(3'-Hydroxymethyl-5'-methyl-4'-picolyl)-5-isopropyl-6-(3'-chloro-5'-methylbenzoyl)-2,4-pyrimidinedione (Compound 77)

Compound 74 obtained in Example 74 (100 mg, 0.21 mmol) was stirred with ammonium hydroxide (0.5 ml) in methanol (5 ml) at room temperature. After 6 hr, the solvent was evaporated in vacuo and the resulting residue was recrystallized from methanol-chloroform to afford 78 mg (yield 85%) of the title compound as a white solid.

M.p.: 238 to 240° C.; $^1$H-NMR (200 MHz, DMSO-d$_6$) δ 1.05 (3H, d, J=6.8 Hz), 1.10 (3H, d, J=6.8 Hz), 2.11 (1H, m), 2.27 (3H, s), 2.49 (3H, s), 4.37 (2H, d, J=5.7 Hz), 4.47 (1H, d, J=17.1 Hz), 4.82 (1H, d, J=17.1 Hz), 5.27 (1H, t, J=5.7 Hz), 6.75 (1H, s), 6.93 (1H, s), 7.56 (1H, s), 7.66 (1H, s), 7.74 (1H, s), 11.63 (1H, s); m/z (EI) 441 (M$^+$).

EXAMPLE 78

Synthesis of 1-(3'-Methoxycarbonyl-4'-picolyl)-5-isopropyl-6-(31,51-dimethylbenzoyl)-2,4-pyrimidinedione (Compound 78)

Compound 62 obtained in Example 62 (100 mg, 0.25 mmol) was stirred with potassium carbonate (138 mg, 1 mmol) and distilled water (0.5 ml) in methanol (5 ml) at room temperature. After 18 hr, the reaction mixture was acidified with glacial acetic acid and the solvent was evaporated in vacuo. The resulting residue was purified by flash chromatography (eluent-ethyl acetate:hexane=4:1) to afford 74 mg (yield 68%) of the title compound as a white solid.

M.p.: 138 to 140° C.; $^1$H-NMR (200 MHz, CDCl$_3$) δ 1.14 (3H, d, J=6.9 Hz), 1.23 (3H, d, J=6.9 Hz), 2.28–2.38 (7H, m), 3.98 (3H, s), 4.68 (1H, d, J=16.0 Hz), 5.00 (1H, d, J=16.0 Hz), 7.21–7.33 (4H, m), 7.73 (1H, s), 8.54 (1H, m), 9.45 (1H, s); m/z (EI) 435 (M$^+$).

EXAMPLE 79

Synthesis of 1-(3'-Carbamoyl-4'-picolyl)-5-isopropyl-6-(3',5'-dimethylbenzoyl)-2,4-pyrimidinedione (Compound 79)

Compound 62 obtained in Example 62 (60 mg, 0.15 mmol)was stirred with conc. sulfuric acid (1 ml) in an oil bath (80° C.). After 10 min, the reaction mixture was allowed to cool to room temperature and poured into distilled water (10 ml). The resulting precipitate was collected by filtration, washed with distilled water and hexane, and dried in vacuo to afford 38 mg (yield 61%) of the title compound as a white solid.

M.p.: 295 to 296° C.; $^1$H-NMR (500 MHZ, DMSO-d$_6$) δ 1.03 (3H, d, J=6.9 Hz), 1.10 (3H, d, J=6.9 Hz), 2.14 (1H, m), 2.25 (6H, s), 4.67 (1H, d, J=17.6 Hz), 4.75 (1H, d, J=17.6 Hz), 7.26 (1H, dd, J=5.0 Hz, J=1.7 Hz), 7.29 (1H, s), 7.53 (2H, s), 7.63 (1H, d, J=2.5 Hz), 7.69 (1H, s), 8.04 (1H, d, J=2.1 Hz), 8.40 (1H, d, J=5.0 Hz), 11.71 (1H, s); m/z (EI) 420 (M$^+$).

EXAMPLE 80

Synthesis of 1-(3'-Carbamoyl-4'-picolyl)-5-isopropyl-6-(3'-chloro-5'-methylbenzoyl)-2,4-pyrimidinedione (Compound 80)

Compound 63 obtained in Example 63 (90 mg, 0.21 mmol) was stirred with conc. sulfuric acid (1 ml) in an oil bath (80° C.). After 10 min, the reaction mixture was allowed to cool to room temperature and poured into distilled water (10 ml). The resulting precipitate was collected by filtration, washed with distilled water and hexane, and dried in vacuo to afford 87 mg (yield 92%) of the title compound as a white solid.

M.p.: 284 to 285° C.; $^1$H-NMR (500 MHz, DMSO-d$_6$) δ 1.03 (3H, d, J=6.8 Hz), 1.10 (3H, d, J=6.8 Hz), 2.12 (1H, m), 2.29 (3H, s), 4.68 (1H, d, J=17.3 Hz), 4.76 (1H, d, J=17.3 Hz), 7.29 (1H, dd, J=5.0 Hz, J=1.7 Hz), 7.58 (1H, s), 7.63 (1H, d, J=2.5 Hz), 7.71 (1H, s), 7.74 (1H, s), 7.80 (1H, s), 8.04 (1H, d, J=2.5 Hz), 8.41 (1H, d, J=5.0 Hz), 11.72 (1H, s); m/z (EI) 440 (M$^+$).

EXAMPLE 81

Synthesis of 1-(4'-Aminobenzyl)-5-isopropyl-6-(3', 5'-dimethylbenzoyl)-2,4-pyrimidinedione (Compound 81)

Compound 38 obtained in Example 38 (50 mg, 0.12 mmol) in methanol (5 ml) was stirred under an atmosphere of hydrogen in the presence of platinium oxide catalyst (10 mg) at room temperature for 4 hr. The reaction mixture was filtered through celite and the solvent was removed under reduced pressure. The resulting residue was purified by flash chromatography (eluent-ethyl acetate:hexane=1:1) to afford 32 mg (yield 70%) of the title compound as a yellow solid.

M.p.: 173 to 175° C.; $^1$H-NMR (200 MHz, CDCl$_3$) δ 1.07 (3H, d, J=6.9 Hz), 1.20 (3H, d, J=6.9 Hz), 2.20–2.40 (7H, m), 3.57 (2H, s), 4.46 (1H, d, J=15.2 Hz), 5.00 (1H, d, J=15.2 Hz), 6.35 (2H, d, J=8.3 Hz), 6.81 (2H, d, J=8.3 Hz), 7.21 (1H, s), 7.26 (2H, s), 8.86 (1H, s); m/z (EI) 391 (M$^+$).

Antiviral Activity and Cytotoxicity Test

The in vitro anti-HIV-1 assays were based on the inhibition of the virus-induced cytopathic effect in MT-4 cells, as described in *J. Med. Chem*, 34, 349 (1991).

First, MT-4 cells were suspended in a culture medium at a concentration of 1×10$^4$ cells/ml and infected with 500 TCID$_{50}$ (50% cell culture infective dose)/well of HIV-1. Immediately after the virus infection, 100 μl of the cell suspension was added to each of the wells of a flat-bottomed microtiter tray containing various concentrations of the test compounds (1) to (81). After incubating for 4 or days at 37° C., the number of viable cells was determined by the 3-(4,5-dimethylthiazol-2-yl)-2,5-diphenyltetrazolium bromide (MTT) method, as disclosed in *J. Virol. Methods*, 20, 309 (1988).

The cytotoxicity of the compounds of the present invention was assessed in parallel with their antiviral activity. It was based on the viability of mock-infected host cells as determined by the MTT method (see J. Virol. Methods, 20, 309 (1988)). MKC-442 (6-benzyl-1-ethoxymethyl-5-isopropyluracil) was employed as a comparative compound.

The results of the tests are shown in Table 4.

TABLE 4

| Ex. No. (Compound) | CD$_{50}$ (μg/ml)* | ED$_{50}$ (μg/ml)** | S.I. (CD$_{50}$/ED$_{50}$)*** |
|---|---|---|---|
| 1 | 22.6 | 0.0026 | 8,600 |
| 2 | 27.2 | 0.0036 | 7,578 |
| 3 | 26.1 | 0.0055 | 4,788 |
| 4 | 64.0 | 0.0027 | 23,940 |
| 5 | 18.7 | 0.012 | 1,553 |
| 6 | 28.2 | 0.0127 | 2,215 |
| 7 | 22.7 | 0.0034 | 6,597 |
| 8 | 28.16 | 0.008 | 3,451 |
| 9 | 40.5 | 0.0119 | 3,401 |
| 10 | 51.7 | 0.0101 | 5,133 |
| 11 | 47.4 | 0.0178 | 2,658 |
| 12 | 38.9 | 0.0542 | 716 |
| 13 | 42.3 | 0.0124 | 3,414 |
| 14 | 29.81 | 0.049 | 612 |
| 15 | 49.87 | 0.053 | 943 |

TABLE 4-continued

| Ex. No. (Compound) | CD$_{50}$ (μg/ml)* | ED$_{50}$ (μg/ml)** | S.I. (CD$_{50}$/ED$_{50}$)*** |
|---|---|---|---|
| 16 | 50.6 | 0.0601 | 841 |
| 17 | 74.3 | 0.112 | 663 |
| 18 | 93.2 | 0.1189 | 784 |
| 19 | 11.28 | 0.003 | 3,394 |
| 20 | 32.9 | 0.012 | 2,758 |
| 21 | 55.07 | 0.0023 | 23,501 |
| 22 | 92.8 | 0.002 | 48,305 |
| MKC-442 | 27.7 | 0.005 | 5,544 |
| 23 | 52.1 | 0.003 | 15,245 |
| 24 | 15.8 | 0.010 | 1,628 |
| 25 | >100 | 0.018 | >5,557 |
| 26 | 6.5 | 0.003 | 2,112 |
| 27 | 8.5 | 0.002 | 5,747 |
| 28 | 12.5 | 0.004 | 3,516 |
| 29 | 44.9 | 1.867 | 24 |
| 30 | 52.3 | 1.935 | 27 |
| 31 | 11.7 | 1.8 | 6 |
| 32 | 40.4 | 0.003 | 12,039 |
| 33 | 57.1 | 0.011 | 5,073 |
| 34 | 37.4 | 0.014 | 2,663 |
| 35 | >100 | 0.0606 | >1,650 |
| 36 | 8.01 | 0.004 | 2,170 |
| 37 | 5.78 | 0.003 | 2,066 |
| 38 | 5.65 | 0.005 | 1,172 |
| 39 | 7.46 | 0.003 | 2,654 |
| 40 | 7.97 | 0.0348 | 229 |
| 41 | 4.63 | 0.009 | 497 |
| 42 | 2.14 | 0.002 | 921 |
| 43 | 7.16 | 0.0035 | 2,057 |
| 44 | 8.17 | 1.80 | 5 |
| MKC-442 | 27.7 | 0.005 | 5,544 |
| 45 | >100 | 0.0098 | >10,170 |
| 46 | 22.9 | 0.0024 | 9,691 |
| 47 | 93.75 | 0.0027 | 35,133 |
| 48 | 12.07 | 0.0030 | 4,021 |
| 49 | 64.39 | 0.0076 | 8,440 |
| 50 | 47.68 | 0.0029 | 16,351 |
| 51 | 17.1 | 0.0010 | 17,812 |
| 52 | 14.3 | 0.0010 | 14,684 |
| 53 | 37.8 | 0.0031 | 12,110 |
| 54 | 8.7 | 0.0017 | 4,992 |
| 55 | 9.9 | 0.0010 | 10,274 |
| 56 | 87.2 | 0.0044 | 19,648 |
| 57 | 9.46 | 0.0028 | 3,411 |
| 58 | 36.03 | 0.0025 | 14,300 |
| 59 | 8.68 | 0.0021 | 4,126 |
| 60 | 17.5 | 0.0026 | 6,739 |
| 61 | 37.5 | 0.0151 | 2,475 |
| 62 | 9.15 | 0.0016 | 5,858 |
| 63 | 8.55 | 0.0029 | 2,966 |
| 64 | 46 | 0.0096 | 4,801 |
| 65 | 44.08 | 0.0075 | 5,916 |
| 66 | >100 | 0.08 | >1,287 |
| MKC-442 | 27.7 | 0.005 | 5,544 |
| 67 | 54.5 | 0.42 | 130 |
| 68 | 56.9 | 0.0145 | 3,928 |
| 69 | 48.25 | 0.0125 | 3,853 |
| 70 | 25.84 | 0.0055 | 4,712 |
| 71 | 25.44 | 0.0082 | 3,092 |
| 72 | 38.49 | 0.0088 | 4,365 |
| 73 | 39.65 | 0.0067 | 5,903 |
| 74 | 28.81 | 0.0134 | 2,152 |
| 75 | 42.06 | 0.0031 | 13,444 |
| 76 | 38.39 | 0.0084 | 4,561 |
| 77 | 23.51 | 0.0115 | 2,052 |
| 78 | 40.79 | 0.0075 | 5,414 |
| 79 | >100 | 0.0091 | >10,942 |
| 80 | 27.83 | 0.0111 | 2,507 |
| 81 | 9.63 | 0.015 | 648 |
| MKC-442 | 27.7 | 0.005 | 5,544 |

Foot note:
*CD$_{50}$: Cytotoxic concentration that causes death of MT-4 cells by 50%
**ED$_{50}$: Effective concentration for the inhibition of the proliferation of HIV-1 by 50%
***S.I.: Selectivity index = (CD$_{50}$/ED$_{50}$)

Antiviral Activity Against Mutant HIV-1

Antiviral activities of the inventive compounds were determined against Y181C which is representative HIV-1 mutant having high resistance against anti-HIV-1 nonnucleosides, e.g., Nevirapine, by the MTT method. MKC-442 was employed as a comparative compound.

The representative results of the tests are shown in Table 5.

TABLE 5

| Compound | $EC_{50}$ $(\mu M)*$ |
|---|---|
| 1 | 0.005–0.014 |
| 4 | 0.010–0.041 |
| MKC-442 | 13.4** |

Foot note:
*$EC_{50}$: Effective concentration for the inhibition of the proliferation of mutant HIV-1 by 50%
**Reference: J. Med. Chem., 42, 4500 (1999)

As the above results show, the novel antiviral 2,4-pyrimidinedione derivatives of the present invention possess high antiviral activity against HIV-1, both wild-type and mutant HIV-1, and at the same time show high selectivity indices, i.e., low toxicity. The inventive compounds can therefore be used as a drug for treating AIDS.

While the invention has been described with respect to the specific embodiments, it should be recognized that various modifications and changes may be made by those skilled in the art to the invention which also fall within the scope of the invention as defined by the appended claims.

What is claimed is:

1. A compound of formula(I) or a pharmaceutically acceptable salt thereof:

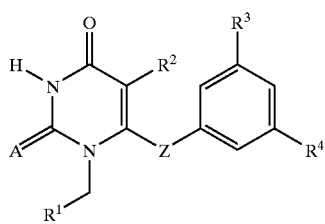

(I)

wherein:

$R^1$ is a phenyl, pyridyl, or N-oxopyridyl group optionally having one or two substituents selected from the group consisting of halogen, $C_{1-6}$ alkyl, $C_{1-6}$ alkyl substituted with one or more halogen atoms, $C_{3-6}$ cycloalkyl, cyano, nitro, hydroxy, thiohydroxy, azido, $C_{1-6}$ alkoxy, $C_{1-6}$ alkylcarbonyl, $C_{3-6}$ cycloalkylcarbonyl, hydroxymethyl, azidomethyl, $C_{1-6}$ alkoxymethyl, $C_{1-6}$ acyloxymethyl, carbamoyloxymethyl, aminomethyl, N—($C_{1-3}$ alkyl)aminomethyl, N,N-di($C_{1-3}$ alkyl) aminomethyl, carboxy, $C_{1-6}$ alkoxycarbonyl, aziridine, amino, hydroxyethylamino, cyclopropylamino, $C_{1-6}$ alkylamino, di($C_{1-6}$ alkyl)amino, trifluoroacetamido, $C_{1-6}$ acylamido, carbamoyl, hydroxyethylcarbamoyl, cyclopropylcarbamoyl, $C_{1-6}$ alkylcarbamoyl, di($C_{1-6}$ alkyl)carbamoyl, aminocarbamoyl, dimethylaminocarbamoyl, hydrazino, 1,1-dimethylhydrazino, imidazolyl, triazolyl and tetrazolyl; a tetrahydropyridyl or piperidyl group optionally substituted with a $C_{1-6}$ alkyl or $C_{1-6}$ alkoxycarbonyl group; a tetrahydropyranyl group; or a tetrahydrofuryl group;

$R^2$ is hydrogen, halogen, nitro, cyano, $C_{1-3}$ alkoxycarbonyl, $C_{1-3}$ alkylamino, di($C_{1-3}$ alkyl)amino, $C_{1-3}$ alkylcarbamoyl, di($C_{1-3}$ alkyl)carbamoyl, $C_{1-6}$ alkyl, $C_{3-6}$ cycloalkyl or benzyl;

$R^3$ and $R^4$ are each independently hydrogen, halogen, hydroxy, cyano, nitro, amino, acetamido, trifluoroacetamido, azido, $C_{1-3}$ alkyl, $C_{1-3}$ alkyl substituted with one or more halogen atoms, $C_{1-3}$ alkoxycarbonyl, carbamoyl, $C_{1-3}$ alkylcarbamoyl, di($C_{1-3}$ alkyl)carbamoyl or $C_{1-3}$ alkoxy;

A is O or S; and

Z is O, C=O, NH or $CH_2$.

2. The compound of claim 1 wherein $R^1$ is a phenyl, pyridyl or N-oxopyridyl group optionally having one or more substituents selected from the group consisting of halogen, $C_{1-3}$ alkyl, $C_{1-3}$ alkyl substituted with one or more halogen atoms, hydroxymethyl, acetoxymethyl, amino, cyclopropylamino, $C_{1-3}$ alkylamino, di($C_{1-3}$ alkyl)amino, trifluoroacetamido, $C_{1-3}$ acylamido, $C_{1-4}$ alkoxy, hydroxy, cyano, azido, nitro, carboxy, $C_{1-4}$ alkoxycarbonyl, carbamoyl, cyclopropylcarbamoyl, $C_{1-4}$ alkylcarbamoyl and di($C_{1-4}$ alkyl)carbamoyl; $R^2$ is halogen, $C_{3-6}$ cycloalkyl or $C_{1-3}$ alkyl; $R^3$ and $R^4$ are each independently hydrogen, halogen, cyano, nitro, amino, trifluoroacetamido, $C_{1-3}$ alkyl, $C_{1-3}$ alkyl substituted with one or more halogen atoms, $C_{1-3}$ alkoxy or $C_{1-3}$ alkoxycarbonyl; A is O or S; and Z is O, S, C=O or NH.

3. The compound of claim 1 wherein $R^1$ is a phenyl, pyridyl or N-oxopyridyl group optionally having one or more substituents selected from the group consisting of methyl, amino, nitro, methoxy, trifluoromethyl, fluoro, bromo, chloro, iodo, cyano, methylamino, ethylamino, isopropylamino, trifluoroacetamido, acetamido, hydroxymethyl, acetoxymethyl, Methoxycarbonyl and carbamoyl; $R^2$ is ethyl or isopropyl; $R^3$ and $R^4$ are each independently hydrogen, chloro, fluoro, bromo, cyano, methyl, ethyl, isopropyl, fluoromethyl, trifluoromethyl, methoxy, amino or nitro; A is O; and Z is O, S, C=O or NH.

4. A process for the preparation of the compound of claim 1 which comprises coupling a compound of formula(II) with a compound of formula(III) in the presence of a base:

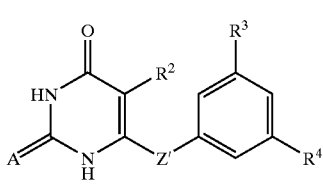

(II)

wherein:

$R^1$, $R^2$, $R^3$, $R^4$ and A have the same meanings as defined in claim 1;

Z' is same as Z defined in claim 1 with the proviso that when A is oxygen, it can be a acetamido group; and Y is halogen, methanesulfonyl, toluenesulfonyl or trifluoromethanesulfonyl.

5. A compound having the formula(II):

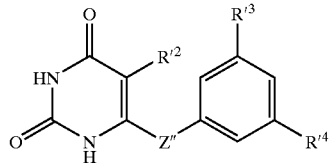

(II)

wherein:

R'² is ethyl or isopropyl;

R'³ is nitro, amino, acetamido, trifluoroacetamido or $C_{1-3}$ alkoxycarbonyl;

R'⁴ is methyl or halogen; and

Z" is C=O, NH or acetamido.

6. An antiviral composition against human immunodeficiency virus (HIV) comprising a therapeutically effective amount of the 2,4-pyrimidinedione compound or a pharmaceutically acceptable salt thereof of claim 1 as an active ingredient, and a pharmaceutically acceptable carrier and/or adjuvant.

\* \* \* \* \*